(12) United States Patent
Lee

(10) Patent No.: US 11,415,332 B2
(45) Date of Patent: Aug. 16, 2022

(54) AIR TREATMENT REACTOR MODULES AND ASSOCIATED SYSTEMS, DEVICES AND METHODS

(71) Applicant: Radic8 PTE LTD, Las Vegas, NV (US)

(72) Inventor: Kang Soo Lee, Seoul (KR)

(73) Assignee: Radic8 PTE LTD, Las Vegas, NV (US)

( * ) Notice: Subject to any disclaimer, the term of this patent is extended or adjusted under 35 U.S.C. 154(b) by 0 days.

(21) Appl. No.: 17/506,634

(22) Filed: Oct. 20, 2021

(65) Prior Publication Data
US 2022/0120458 A1 Apr. 21, 2022

(30) Foreign Application Priority Data
Oct. 21, 2020 (KR) .................. 10-2020-0137057

(51) Int. Cl.
*F24F 8/22* (2021.01)
*F24F 8/80* (2021.01)
(Continued)

(52) U.S. Cl.
CPC ............ *F24F 8/22* (2021.01); *B01J 19/0053* (2013.01); *B01J 19/123* (2013.01); *F24F 8/80* (2021.01);
(Continued)

(58) Field of Classification Search
CPC .................. F24F 8/22; F24F 8/80; A61L 9/20
See application file for complete search history.

(56) References Cited

U.S. PATENT DOCUMENTS

| 7,674,436 B1 * | 3/2010 | Feldman ................. A61L 9/205 55/482 |
| 2006/0057020 A1 * | 3/2006 | Tufo ......................... A61L 9/20 422/24 |

(Continued)

FOREIGN PATENT DOCUMENTS

| JP | 6008423 B2 | 10/2016 |
| KR | 100891128 B1 | 4/2009 |

(Continued)

OTHER PUBLICATIONS

International Application No. PCT/US2021/055923—International Search Report and Written Opinion dated Feb. 10, 2022, 12 pages.
(Continued)

*Primary Examiner* — Kevin Joyner
(74) *Attorney, Agent, or Firm* — Perkins Coie LLP

(57) ABSTRACT

Embodiments of the present technology are directed to air treatment reactor modules, and associated systems and devices. An exemplary reactor module can include a housing, an ultraviolet (UV) light source disposed within the housing, and a plurality of hollow elongate conduits disposed within the housing and peripheral to the UV light source. The UV light source and individual conduits can extend in a lateral direction perpendicular to the direction of air flow through the reactor module. The conduits can include a plurality of holes and be at least partially coated with a photocatalytic material. The housing can have an inner surface comprising a reflective material that, in operation, reflects UV light emitted from the UV light source.

30 Claims, 23 Drawing Sheets

(51) Int. Cl.
    *A61L 9/20*     (2006.01)
    *B01J 19/12*     (2006.01)
    *B01J 19/00*     (2006.01)

(52) U.S. Cl.
    CPC .. *B01J 2219/024* (2013.01); *B01J 2219/0892* (2013.01); *B01J 2219/1928* (2013.01)

(56) References Cited

U.S. PATENT DOCUMENTS

| | | | |
|---|---|---|---|
| 2007/0217969 A1* | 9/2007 | Cheng | A61L 9/22 422/186.3 |
| 2010/0143205 A1* | 6/2010 | Engelhard | A61L 9/00 422/121 |
| 2011/0011112 A1 | 1/2011 | Goel et al. | |
| 2012/0070335 A1* | 3/2012 | Carey | A61L 9/205 422/4 |
| 2016/0213803 A1* | 7/2016 | Lunman | A61L 9/20 |
| 2020/0049373 A1 | 2/2020 | Huang | |

FOREIGN PATENT DOCUMENTS

| | | |
|---|---|---|
| KR | 20180055984 A | 5/2018 |
| WO | 2012117547 A1 | 9/2012 |
| WO | 2018016115 A1 | 1/2018 |

OTHER PUBLICATIONS

Kim, Myung Sook, "Reactor Module having sterilization honeycomb panel and Air sterilizer included reactor module," Published Jan. 21, 2022, Registration No. KR1023545650000, 19 pages.

* cited by examiner

AIR TREATMENT REACTOR MODULES AND ASSOCIATED SYSTEMS, DEVICES AND METHODS

CROSS-REFERENCE TO RELATED APPLICATION(S)

The present application claims the benefit of and priority to Korean Patent Application No. 10-2020-0137057, filed Oct. 21, 2020, the disclosure of which is incorporated herein by reference in its entirety.

TECHNICAL FIELD

The present disclosure relates to air treatment reactor modules and associated systems, devices and methods.

BACKGROUND

Individuals spend more than 90% of their time indoors and, as such, indoor air quality management and infection control (e.g., of respiratory diseases) are of great significance to public life and health. Existing air treatment devices provide purified air but suffer from multiple deficiencies, including being too expensive, requiring constant maintenance, producing noise above acceptable levels, having limited air treatment efficiency, and drawing significant power, amongst other deficiencies. Accordingly, there exists a need for an improved air treatment device for purifying, filtering, and/or at least partially sterilizing indoor air environments.

BRIEF DESCRIPTION OF THE DRAWINGS

Features, aspects, and advantages of the presently disclosed technology may be better understood with regard to the following drawings.

Figure 1A:
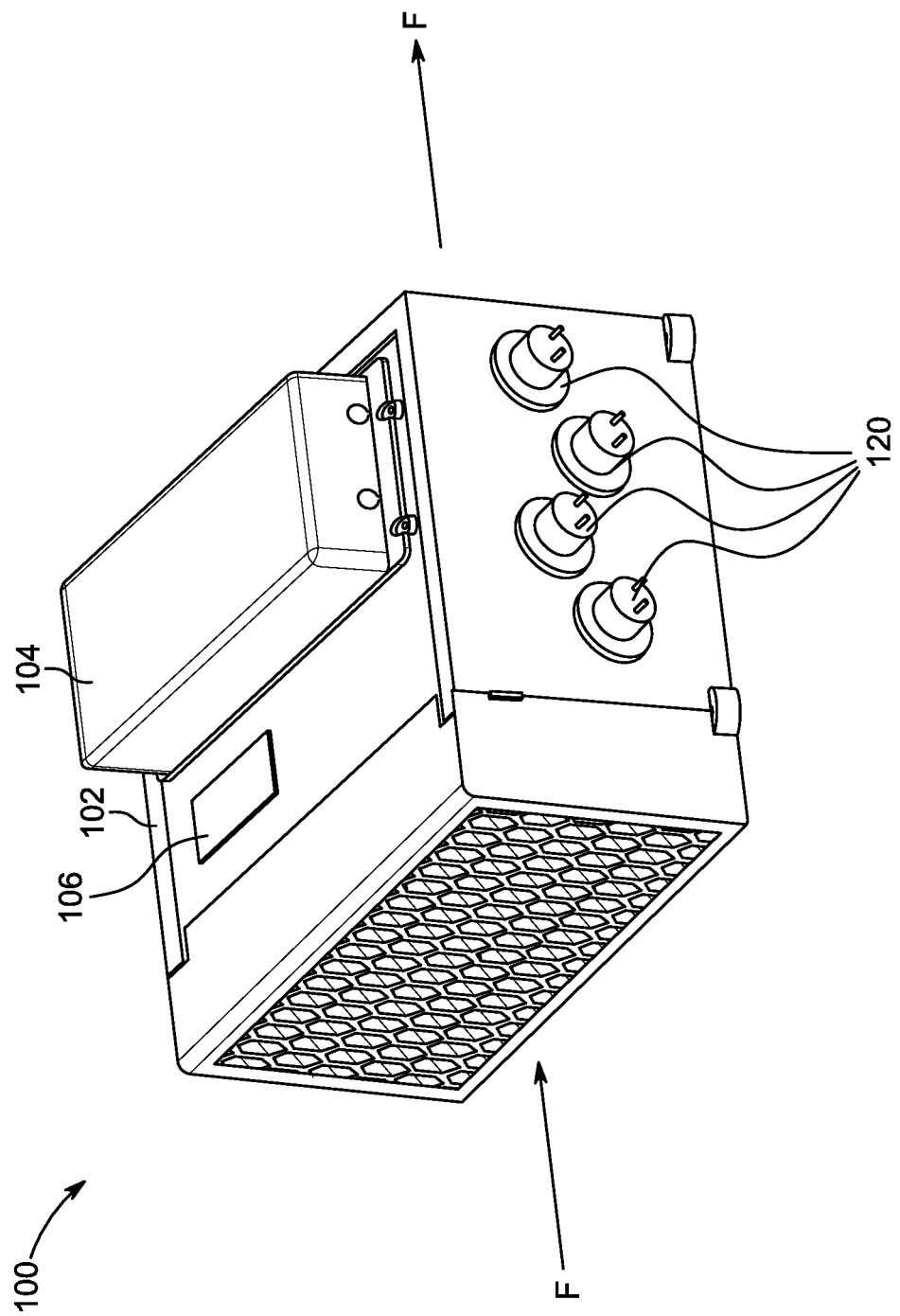
FIG. 1A is a partially schematic isometric view of a reactor module of an air treatment device, in accordance with embodiments of the present technology.

In the Figures, identical reference numbers identify generally similar, and/or identical, elements. Many of the details, dimensions, and other features shown in the Figures are merely illustrative of particular embodiments of the disclosed technology. Accordingly, other embodiments can have other details, dimensions, and features without departing from the spirit or scope of the disclosure. In addition, those of ordinary skill in the art will appreciate that further embodiments of the various disclosed technologies can be practiced without several of the details described below.

DETAILED DESCRIPTION

I. Overview

Current air treatment devices suffer from multiple deficiencies including excess noise output and limited air treatment efficiency. For example, current air treatment devices either cannot sterilize all or even a majority of the air that travels through the devices, or, in order to sterilize a majority of the air, the devices are designed to have a relatively limited air volume throughput. This is in part due to the shape and dimensions of the housing of reactor modules, the presence (or lack thereof) and relative positioning of photocatalytic surfaces, and/or the arrangement and positioning ultraviolet light sources relative to the photocatalytic surfaces and the direction of air flow through the housing.

Embodiments of the present technology at least partially mitigate these and other deficiencies by providing reactor modules and/or air treatment devices/systems that are able to effectively treat (e.g., sterilize, filter, and/or purify) air to provide treated indoor environments substantially free of undesirable contaminants. An exemplary reactor module of the present technology can include a housing configured to pass air flow from an inlet to an outlet of the housing, one or more elongate ultraviolet (UV) light sources disposed within the housing, and a plurality of elongate conduits disposed within the housing and that at least partially surround or sandwich the UV light sources. The UV light sources can be configured to emit UVC light radially outwardly in all directions. The housing can have a rectangular shape with a length dimension along the direction of air flow, and a width dimension that in some embodiments is longer than the length dimension. As explained elsewhere herein, the shape and dimensions of the housing can be designed to optimize residence time of air contaminants in the reactor module to ensure treatment (e.g., sterilization) rates are above a predetermined rate, while also maximizing or maintaining design air throughput volumes.

Individual conduits of the reactor modules can extend in a lateral direction perpendicular to the direction the air flow through the reactor module, and can be grouped in sets (e.g., rows or columns) that extend either along the direction of airflow through the housing or along a height of the housing. Arranging the conduits in such a manner relative to the air flow can optimize contact between the conduits and the air flow, or more particularly the contaminants of the air. In some embodiments, the conduits can be a hollow structure with an outer surface that includes a plurality of holes, e.g., having hexagonal, honeycomb, triangular, square, rectangular, polygonal, or other shapes. The conduits can be coated with a photocatalyst or other material configured to enable sterilization of the incoming air, e.g., by forming, in combination with the UV light sources, hydroxyl free radicals that react with the contaminants on the surface of the conduits.

In some embodiments, the reactor modules can include a panel member, e.g., at an inlet or intermediate region of the housing, to provide further treatment of the incoming air. The panel member can extend along an entire width and height of the housing, and can include a plurality of holes that define channels or air paths through the panel member. The channels are configured to receive the incoming air and can help distribute the incoming air across a cross-sectional area of the housing, e.g., to ensure the air reaches peripheral regions of the housing and does congregate in an intermediate region. The panel member can be coated with a photocatalyst that can further contribute to sterilizing the incoming air.

In some embodiments, other components can be coupled to the reactor module to improve treatment of the incoming air or operation of the reactor module. For example, a wind guide assembly and/or a treatment module can be coupled to the reactor modules, e.g., downstream of the conduits and UV light sources. The wind guide assembly can mitigate undesirable noise output from the reactor module, and/or reduce turbulence of the treated air flow from the reactor module and enable the air flow to have a laminar flow profile. The treatment module can also mitigate undesirable noise output from the reactor module.

One or more of the reactor modules can be incorporated into an air treatment device or system configured to operate as a stand or stand-up device, or mounted to a ceiling, duct or wall. As described elsewhere herein, the air treatment systems can include other components, including one or more filters and/or fans.

II. Modules and Systems for Purifying and/or Sterilizing Air

FIG. 1A is a partially schematic isometric view of a reactor module 100, in accordance with embodiments of the present technology. As described elsewhere herein, the reactor module 100 can be configured to be incorporated into a device and/or system configured to treat (e.g., filter and/or sterilize) air and filter or remove undesirable contaminants con, such as dust, viruses, bacteria, mold, fungi, allergens, volatile organic compounds (VOCs), fumes, and odors. As shown in FIG. 1A, the reactor module 100 includes a housing 102, a plurality of ultraviolet (UV) light sources 120 disposed within the housing 102, a power source 104 operably coupled to the UV light sources 120, and a controller 106 operably coupled to the power source 104 and/or the UV light sources 120. The controller 106 can couple the power source 104 to the UV light sources 120 and thereby control lighting of the UV light sources. The controller 106 can also be configured to operate the reactor module 100 in one or more operating modes. Factors for determining an operating mode for the reactor module 100 can depend on the end use of the reactor module 100, and may include the desired purified and/or sterilized air throughout, noise output, module orientation, and air filtration, amongst other factors. The UV light sources 120 can include UVC light sources (e.g., wavelengths from about 100-280 nm), UVA light sources (e.g., wavelengths from about 315-400 nanometers (nm)), UVB light sources (e.g., wavelengths from about 280-315 nm), and combinations thereof.

Figure 1B:
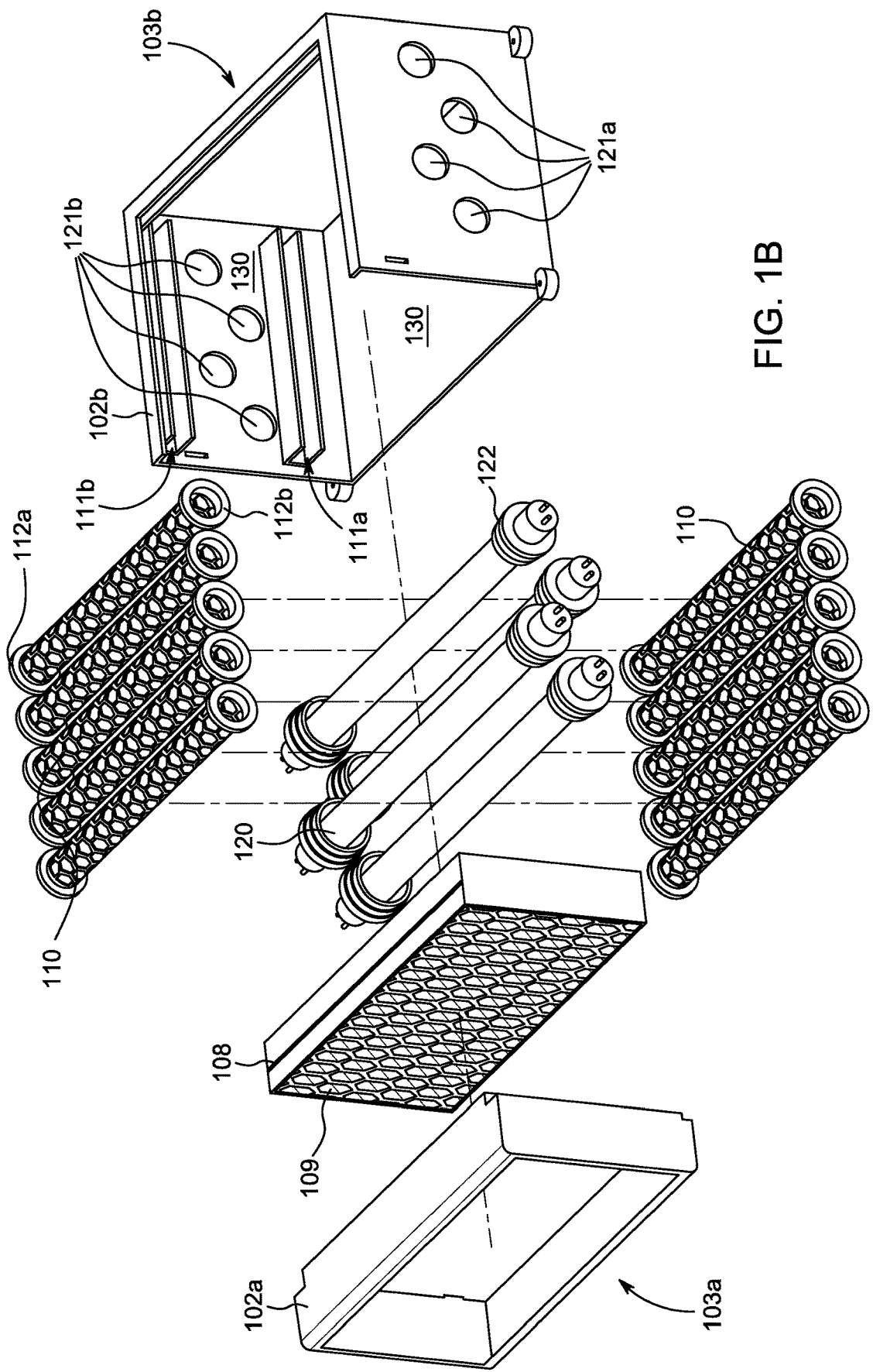
FIG. 1B is a partially exploded isometric view of the reactor module of FIG. 1A.

FIG. 1B is a partially exploded isometric view of the reactor module 100 of FIG. 1A. For illustrative purposes, portions of the reactor module 100 (e.g., the top cover of the reactor module 100) have been removed from FIG. 1B. As shown in FIG. 1B, the reactor module 100 includes the housing 102 previously described, which includes a first housing portion 102a defining an inlet 103a at a proximal end of the reactor module 100 and a second housing portion 102b defining an outlet 103b at a distal end of the reactor module 100. The first housing portion 102a can be mechanically coupled the second housing portion 102b to form a single piece containing individual components of the reactor module 100. The first housing portion 102a and the second housing portion 102b are collectively referred to herein as the housing 102. The housing 102 can have a rectangular shape such that a length of the housing 102 (e.g., defining a first axis) along the primary direction of air flow between the inlet 103a and the outlet 103b is greater than a lateral width (e.g., defining a second axis), and in some embodiments a height (e.g., a third axis), of the reactor module 100. In such embodiments, the pressure drop of air is decreased, relative to a reactor module having a length along the primary direction of air flow that is longer than a width of the reactor module, The length of the housing 102 can affect a residence time of the air flowing through the reactor module 100 and thus can be adjusted depending on end use and related factors (e.g., desirable air throughput and/or sterilization). For example, the length of the housing 102, and therein the reactor module 100, can be increased to accommodate a higher sterilization power, air volume throughput, and/or air flow rate. Additionally or alternatively, the length of the housing can affect (i) pressure drop of air flowing through the reactor module 100, with a longer length being correlated to a larger pressure drop, and (ii) the laminar flow profile of the air exiting the reactor module at the outlet 103b, with a longer module being correlated to more laminar flow. In some embodiments, the housing 102 can comprise other shapes (e.g., a cylindrical shape), based on the desired end use of the corresponding air treatment device.

The reactor module 100 can further include a panel member 108, the plurality of UV light sources 120 previously described, and a plurality of conduits 110. Individual ones of the UV light sources 120 and the conduits 110 can extend laterally within the housing 102 along the second axis and are thus perpendicular to the direction of air flow through the reactor module along the first axis from the inlet 103a to the outlet 103b. Positioning the conduits 110 in such an arrangement relative to the air flow can enable more air to contact the conduits 110, compared to if the conduits 110 were parallel to the air flow. As described elsewhere herein, this can improve air treatment efficiency of the reactor module 100. In some embodiments, such as the illustrated embodiment of FIG. 1B, the conduits 110 can be arranged in rows that are disposed along a length or first axis of the reactor module 100 or direction of airflow through the reactor module 100. As explained elsewhere herein (e.g., with reference to FIG. 4), the rows of conduits 110 can be arranged along a height or third axis of the reactor module 100 and be angled and/or perpendicular to the director of air flow. Such arrangement of the conduits 110 can allow for ample air flow through the reactor module 100, while also providing ample contact of the air flowing through the reactor module 100 with the surface of the conduits 110. The conduits 110 can be disposed at least partially around (e.g., above and below, proximal and distal, and/or radially) the UV light sources 120. For example, the conduits 110 can include a first row of conduits 110 disposed peripheral to the UV light sources 120 in a first direction (e.g., an upward direction) and a second row of conduits 110 disposed peripheral to the UV light sources 120 in a second direction (e.g., a downward direction) different or opposite the first direction. Stated differently, the UV light sources 120 can be positioned in an intermediate region (e.g., not at the top or bottom regions) of the housing 102, and the conduits 110 can be positioned in a peripheral region of the housing 102 radially outward of the UV light sources 120 and the intermediate region. Disposing the UV light sources 120 radially inward of the conduits 110, as opposed to outward, can beneficially ensure that more or substantially all or a majority of the air flow through the housing 102 is sterilized via light from the UV light sources 120. Additionally or alternatively, disposing the conduits 110 close to one another (e.g., abutting one another) and radially outward of the UV light sources 120 (e.g., both above and below the UV light sources 120) can help ensure UV rays emanated from the UV light sources 120 are inhibited or prevented from emanating outside the housing 102. That is, the structure of the conduits 110 can physically block the UV rays from emanating therebeyond. The conduits 110 are described in additional detail in FIGS. 2A and 2B.

The conduits 110 and the UV light sources 120 can be fixedly coupled to the housing 102, or more particularly to the second housing portion 102b. As shown in FIG. 1B, the second housing portion 102b can include holes 121a/b on opposing sidewalls of the second housing portion 102b that are configured to receive the UV light sources 120. The UV light sources 120 can include coupling members 122 made from rubber or other flexible materials to fix individual UV light sources 120 in place, as well as ensure UV light emanating therefrom is inhibited from or does not pass through the holes 121a/b and expose users of the corresponding air treatment devices. The UV light sources 120 can be horizontally and/or vertically staggered relative to one another. For example, as shown in FIG. 1B, the UV light sources 120 can include a first most proximal UV light source, a second UV light source distal to and vertically offset (i.e., above) from the first UV light source, a third UV light source distal to and vertically offset (i.e., below) from the second UV light source, and a fourth UV light source distal to and vertically offset (i.e., above) from the third UV light source. Staggering the UV light sources can ensure more light is emitted therefrom and increase the likelihood of the light contacting the incoming air.

As also shown in FIG. 1B, the second housing portion 102b can include one or more elongate trays or holders 111a/b for receiving (e.g., fixing, securing, holding, etc.) the conduits 110. The holders 111a/b are positioned radially outward of the holes 121a/b. In some embodiments, the holders 111a/b and housing 102 are formed together, such that they constitute a single piece with a continuous surface. Individual holders 111a/b can extend along a side of the housing 102 along the direction of air flow or first axis through the reactor module 100. In some embodiments, the holders 111a/b comprise only a single protruding lip spaced apart from an upper or lower surface of the second housing portion 102b. The holders 111a/b can be generally positioned near an upper or lower region of the side of the housing 102 such that the conduits 110 can be secured within the holders 111a/b between an upper or lower surface of the housing 102 and a protruding lip of the holders 111a/b. In some embodiments, the conduits can include couplers (e.g., bosses) 112a/b at opposing end portions of the conduits 110, which can have a dimension slightly smaller than a corresponding dimension of the holders 111a/b such that the holders can receive the couplers 112a/b and maintain them in a fixed position during operation of the reactor module 100. In doing so, the conduits 110 may not be in physical contact with the lip of the holders 111a/b or the upper or lower surface of the housing 102, which may beneficially prevent the conduits 110 from being damaged, and/or enable more surface area of the conduits 110 to be exposed and allow more efficient air treatment. In some embodiments, the couplers 112a/b are rotatably coupled to the end portions of each conduit 110. As shown in FIG. 1B, the reactor module 100 includes two rows of conduits 110 and the housing 102 includes two corresponding holders 111a/b. In other embodiments, the reactor module 100 can include additional rows of conduits 110 and the housing 102 can include additional corresponding holders 111a/b. Relatedly, the illustrated embodiment includes five conduits 110 per row. In other embodiments, the number of conduits 110 of each row can be more or less, e.g., depending on the required air throughput of the reactor module 100.

The panel member 108 can be proximate the inlet 103a and proximal to the UV light sources 120 and/or conduits 110. The panel member 108 can comprise aluminum, plastic, and/or other semi-rigid materials. In some embodiments, including the illustrated embodiment of FIG. 1B, the panel member 108 can span an entire height and/or lateral width of the housing 102 such that all or a majority of air flowing through the reactor module 100 passes through the panel member 108. As explained elsewhere herein (e.g., with regard to FIGS. 5A and 5B), the panel member 108 can include a plurality of holes or openings 109 extending through the panel member 108, each defining a channel or path for air to flow through. The holes 109 can have a circular, ovular, hexagonal, or other shape configured to increase an exposed surface area for the air flowing therethrough to contact. The panel member 108 and/or holes 109 provide multiple benefits to the reactor module 100. For example, the panel member 108 can entirely or partially block UV light emitted from the UV light source 120 from emanating proximally of the panel member 108 and thus exposing a user to such UV light. As another example, the holes 109 can cause air flow to be more evenly distributed across a height and/or width of the panel member 108, e.g., to upper, lower and/or lateral end portions of the panel member 108, which can help ensure air flow is not concentrated in an intermediate region of the reactor module 100. Distributing the air flow in such a manner can enable more air to be treated and thus improve contaminant removal efficiency.

In some embodiments, the panel member 108 and/or the holes 109 of the panel member 108 can comprise a catalyst and/or photocatalytic material, such as titanium dioxide (e.g., pure titanium dioxide), or titanium dioxide doped with (i) metals ions such as noble metals (Au, Pd, Pt), (ii) rare earth metals (Sc, Y) transition metals (Mn, Fe, Cu), or (iii) non-metals ions such as carbon, nitrogen or sulphur. Combinations thereof are also possible. For example, a first portion of the panel member may comprise pure titanium dioxide and a second, different portion may comprise titanium dioxide doped with a rare earth metal. In some embodiments, the photocatalytic material can comprise a porous material such as organic ligands, metal-organic frameworks (MOFs), and/or cage molecules. Such porous materials can include a central cavity void sized to selectively target and remove undesirable contaminants (e.g., the contaminants disclosed elsewhere herein) from the air. In such embodiments, all or portions of the panel member 108 can be coated with the catalyst(s) and/or photocatalytic material(s). In operation, air flow through the panel member 108 can sterilize the air, or enable the air becoming sterilized, e.g., by removing certain contaminants such as viruses, bacteria, mold, fungi, and allergens, amongst other contaminants. For example, the catalyst can cause hydroxyl radicals to form on surfaces of the panel member 108 which, in combination with the UV light sources 120, can enable these contaminants to be removed. In some embodiments, the panel member 108 can be omitted. In other embodiments, multiple panel members 108 can be included. For example, when multiple panel members 108 are included, the panel members 108 can be proximate (e.g., abut) one another and proximal to the UV light sources 120. As another example, one panel member 108 can be proximal to the UV light sources 120 adjacent the inlet 103a and another panel member 108 can be distal to the UV light sources 120 adjacent the outlet 103b.

As explained in additional detail elsewhere herein (e.g., with reference to FIGS. 6A and 6B), the housing 102 can include an interior surface 130 that comprises or is at least partially coated with a reflective material (e.g., chrome or chromium). Such a material can help ensure the UV rays emanated from the UV light sources 120 are reflected and maintained within the housing 102 and/or not radiated outside the housing 102. In doing so, the reactor module 100 can more efficiently destroy contaminants, as the likelihood that UV wavelengths emanated from the UV light sources come in contact with and destroy contaminants is increased.

Figure 2A:
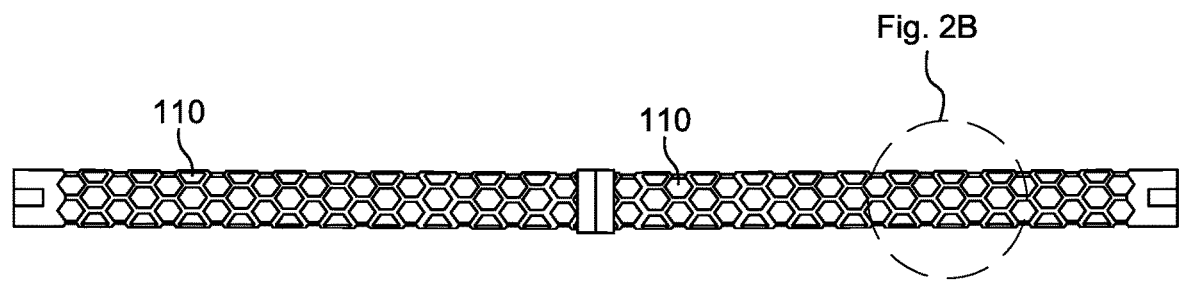
FIGS. 2A and 2B are side views of conduits of a reactor module, in accordance with embodiments of the present technology.
Figure 2B:
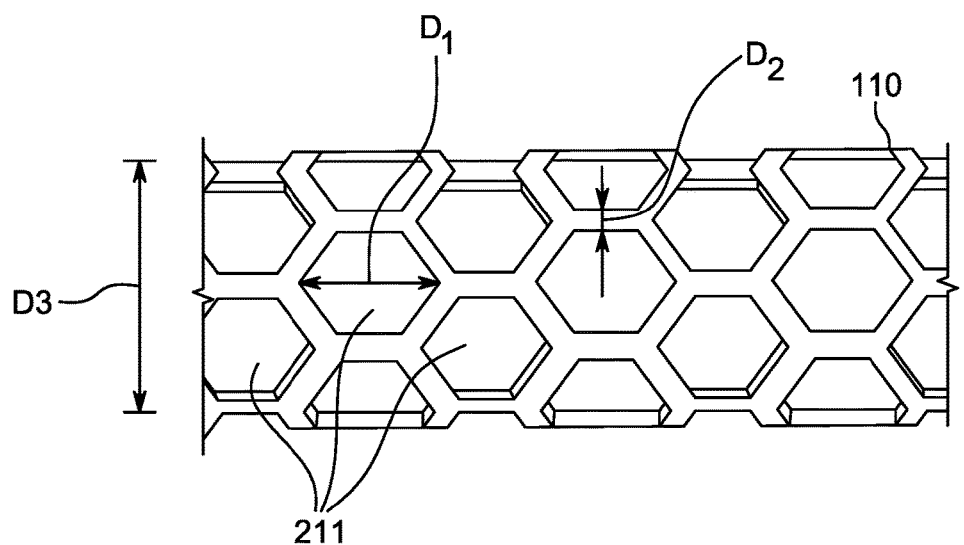

FIGS. 2A and 2B are side views of the conduits 110 of the reactor module of FIG. 1A. All or portions of the conduits 110 can comprise and/or be coated with a catalyst and/or photocatalytic material such as titanium dioxide (e.g., pure titanium dioxide), or titanium dioxide doped with (i) metals ions such as noble metals (Au, Pd, Pt), (ii) rare earth metals (Sc, Y) transition metals (Mn, Fe, Cu), or (iii) non-metals ions such as carbon, nitrogen or sulphur. Combinations thereof are also possible. For example, one of the conduits 110 may comprise pure titanium dioxide and a another one of the conduits 110 may comprise titanium dioxide doped with a rare earth metal. In some embodiments, the titanium dioxide can comprise rutile titanium dioxide and/or anatase titanium dioxide, and/or the titanium dioxide can comprise less than 5%, 4%, 3%, 2.5%, or 2% by weight of the solution. Additionally or alternatively, in such embodiments including titanium dioxide, the amount of anatase titanium dioxide can be at least 60%, 65%, 70%, 75%, 80%, 85%, or 90% by weight, with the balance being rutile titanium dioxide. In some embodiments, the amount of anatase titanium dioxide can be within a range of 60-90%, 65-80%, 65-75%, or 68-72% by weight, with the balance being rutile titanium dioxide. The catalyst and/or photocatalytic material can be applied to the conduits via spray or dip coating, as described elsewhere herein (e.g., with reference to FIG. 3). In such embodiments, all or portions of the conduits 110 can comprise and/or be coated with the catalyst(s) and/or photocatalytic material(s).

In operation and without being bound by theory, when the photocatalytic material receives light wavelength less than about 387 nm (e.g., UVA, UVB and/or UVC wavelengths) photoactivation of the photocatalytic material occurs and results in semiconductor properties. Specifically, the light wavelengths cause the valence band of the photocatalytic material to lose an electron, enabling the valence band to react with water in the air to produce hydroxyl radicals. Additionally, electrons lost from the valence band can react with oxygen in the air to form oxide anions. The radicals exist on the surfaces comprising the photocatalyst material, and react with and remove and/or deactivate contaminants (e.g., viruses, bacteria, mold, fungi, VOCs, gases, and allergens) from the air via photocatalytic oxidation (PCO).

Referring to FIGS. 2A and 2B together, the conduits 110 are hollow and can have an outer surface that defines a plurality of openings 211. In some embodiments, the length of an individual conduit 110 can be increased and/or multiple conduits can be connected to one another end-to-end as shown in FIG. 2A, e.g., to be able to treat a higher air flow through the reactor module 100 (FIGS. 1A and 1B). As shown in FIGS. 2A and 2B, the conduits 110 can have a cylindrical shape and thus be round, which can enable the conduits 110 to have a larger PCO reaction area, relative to a square pillar or a plate having the same openings. The conduits 110 can comprise plastic and be formed via injection molding. In some embodiments, the conduits 110 do not comprise metal.

In some embodiments, the openings 211 of the conduits 110 can have a hexagonal or honeycomb shape, as shown in FIGS. 2A and 2B, which can increase an exposed surface area for contaminants of the air to come in contact with. Advantageously, the hexagonal shape enables each individual opening 211 to complement each other hexagonal opening 211, as the border of each hexagonal opening 211 forms part of the border of a neighboring hexagonal opening 211, while also maintaining a sufficiently large opening 211. In doing so, as shown in FIG. 2B, a first dimension ($D_1$) of each opening 211 can be maximized and a second dimension ($D_2$) defining a border between neighboring openings 211 can be minimized. The first dimension ($D_1$), the second dimension ($D_2$), and a third dimension ($D_3$) corresponding to diameter of cross-sectional dimension of the conduits 110, can be predetermined and selected to optimize PCO reaction area of the conduits 110, while also ensuring the conduits 110 can treat enough air to support the design air volume throughput of the reactor module 100. In some embodiments, the first dimension ($D_1$) can be no more than 11 millimeters (mm), 10 mm, 9 mm, 8 mm, or 7 mm or within a range of 7-11 mm, or 8-10 mm. In some embodiments, the second dimension ($D_2$) can be no more than 6 mm, 5 mm, 4 mm, 3 mm, or 2 mm, or within a range of 2-6 mm, or 3-5 mm. In some embodiments, the third dimension ($D_3$) can be no more than 20 mm, 18 mm, 16 mm, 14 mm, or 12 mm, or within a range of 12-20 mm, or 14-18 mm. In some embodiments, the openings 211 of the conduits 110 can have a triangular, circular, rectangular, polygonal, or shape other than a hexagonal or honeycomb.

Figure 3:
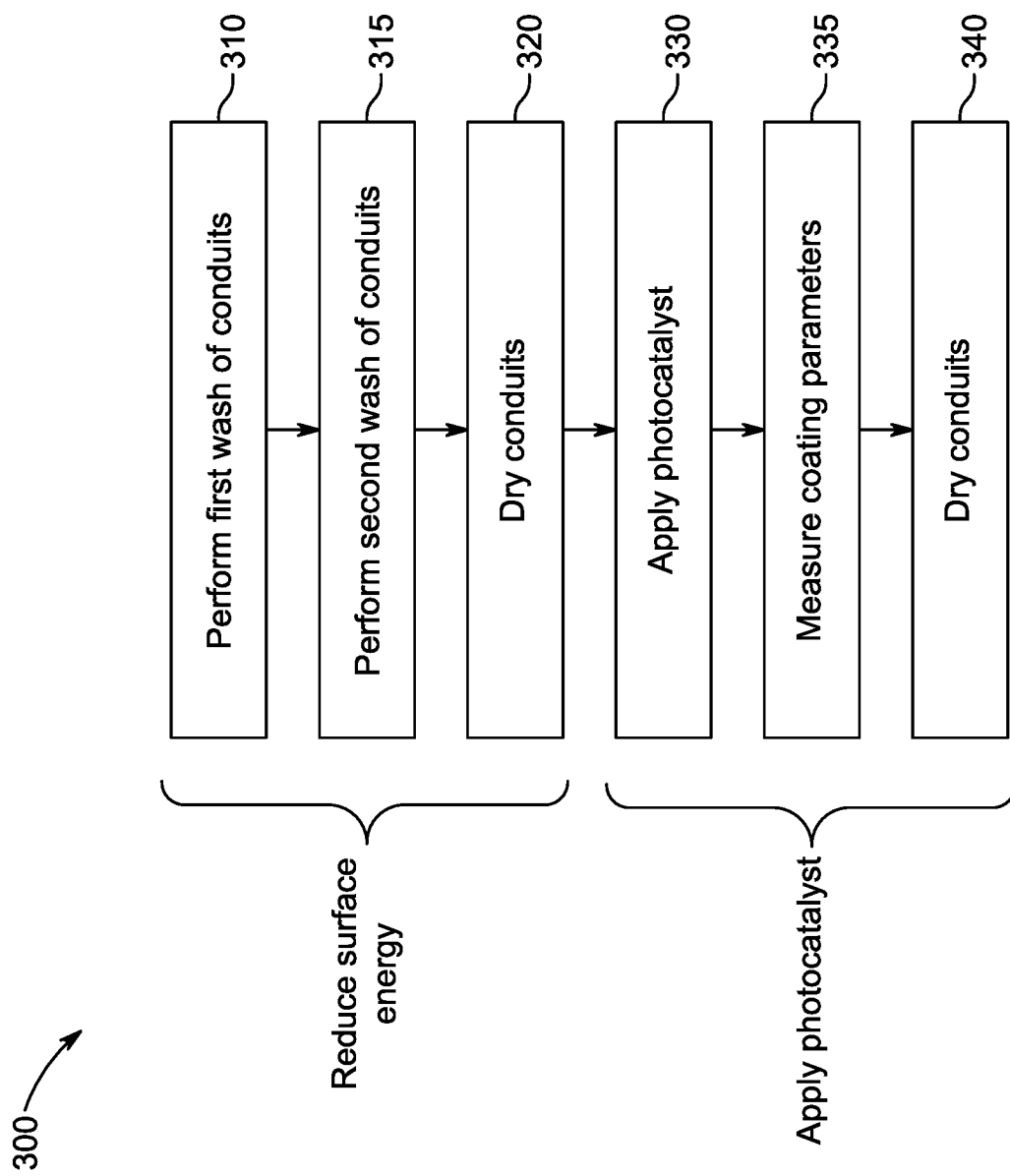
FIG. 3 is a flow diagram of a method for applying photocatalyst to conduits used in a reactor module, in accordance with embodiments of the present technology.

FIG. 3 is a flow diagram of a method 300 for pre-treating conduits (e.g., the conduits 110) of a reactor module (e.g., the reactor module 100). As previously described, a photocatalyst can be applied to the conduits to promote PCO of contaminants of the air flowing through the reactor module. Prior to applying the photocatalyst, it can be advantageous to first reduce the surface tension of the conduits such that wettability or hydrophilicity of the conduits is increased and the spread ability of the photocatalyst is improved. After washing the conduits, the photocatalyst, once applied to the conduits, can appropriately harden and therein have a more pronounced photocatalytic oxidative effect during operation of the reactor module.

The method 300 can include performing a first wash of the conduits (process portion 310). The first wash can include ultrasonic washing with water (e.g., distilled water), in which the conduits are washed using ultrasonic waves (e.g., 20-40 kilohertz waves). This removes impurities from the conduits and therein reduces the surface tension of the conduits which, as previously described, can improve wettability and hydrophilicity. The method 300 can optionally include performing a second wash of the conduits after the first wash (process portion 315). The second wash can be identical to the first wash, and can ensure more or all impurities are removed from the conduits and the surface tension is minimized prior to applying a photocatalyst. The method 300 can further include drying the conduits (process portion 320) at a predetermined temperature and/or for a predetermined amount of time, to remove any moisture therefrom. In some embodiments, at this point the surface tension may be measured prior to proceeding to apply photocatalyst on the conduits. For example, in some embodiments the contact angle of the surface of the conduits is measured using a liquid (e.g., water or diiodomethane), and based on the contact angle and surface tension of the liquid, surface tension is determined. In some embodiments, a contact angles less than 15°, 10°, or 5° is considered an acceptable angle that indicates surface tension has been sufficiently reduced and photocatalyst is ready to be applied.

The method 300 further includes, after reducing the surface tension of the conduits, applying photocatalyst to the conduits (process portion 330). The photocatalyst can include titanium dioxide (e.g., pure titanium dioxide), or titanium dioxide doped with (i) metals ions such as noble metals (Au, Pd, Pt), (ii) rare earth metals (Sc, Y) transition metals (Mn, Fe, Cu), or (iii) non-metals ions such as carbon, nitrogen or sulphur. Combinations thereof are also possible. The photocatalyst can be applied via spray coating or dip coating. With spray coating, the photocatalyst is applied evenly over the base material and, due in part to the surface tension tension of the conduits being reduced, can spread naturally over the entire conduit to ensure the surface area of the conduits is substantially covered.

The method 300 can further include measuring coating parameters (process portion 335), e.g., to determine the effectiveness of process portion 330. The method 300 can further include drying the conduits after applying the photocatalyst (process portion 340) at a predetermined temperature and/or for a predetermined amount of time, to remove any moisture therefrom.

Figure 4A:
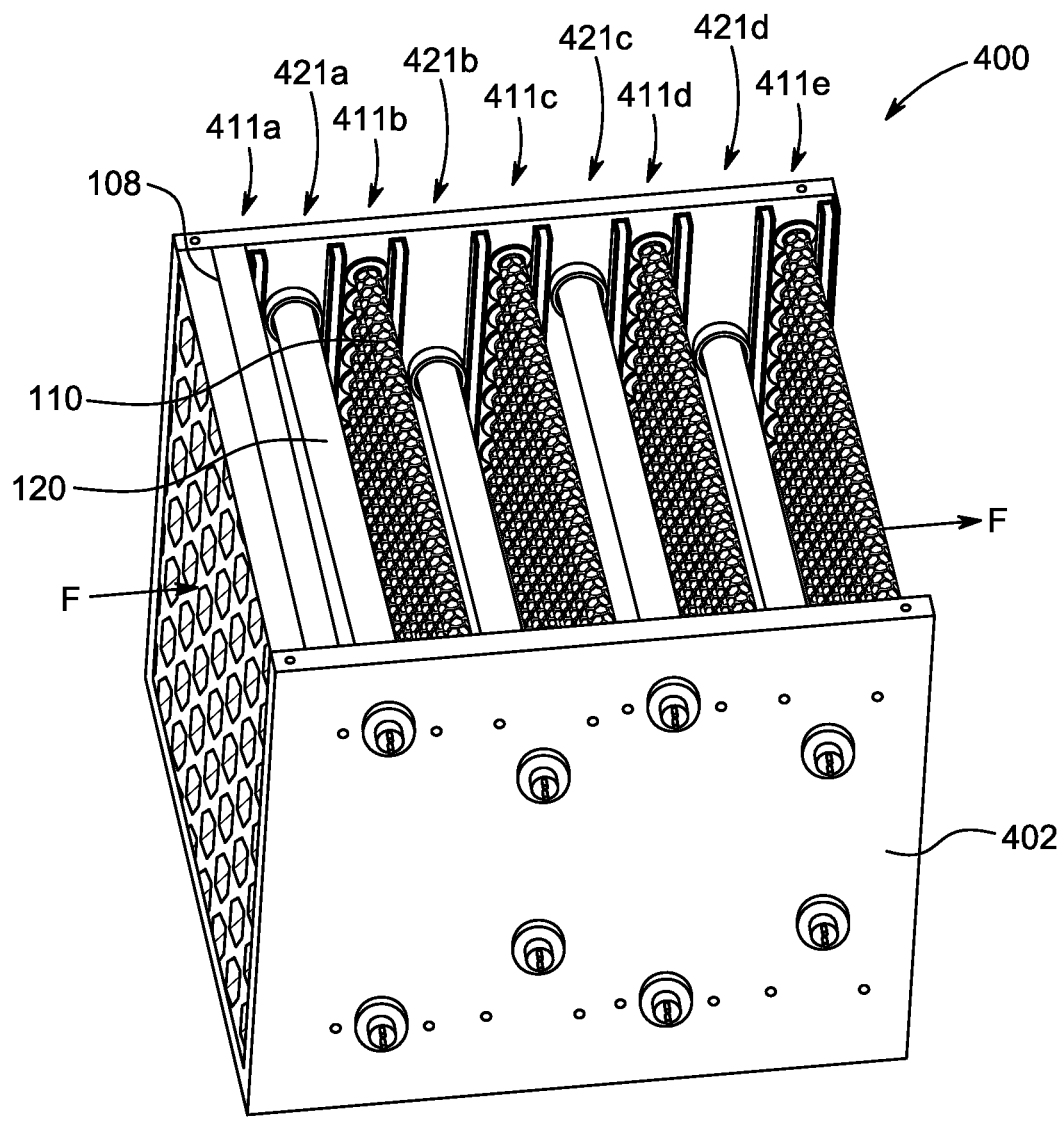
FIGS. 4A and 4B are partially schematic views of other reactor modules, in accordance with embodiments of the present technology.

FIG. 4A is a partially schematic view of another reactor module 400, in accordance with embodiments of the present technology. For illustrative purposes, the top sidewall of the housing 402 has been removed from FIG. 4A. The reactor module 400 includes many of the same components as reactor module 100 described with reference to FIGS. 1A and 1B. For example, the reactor module 400 includes the panel member 108, conduits 110, and UV light sources 120 previously described. Unlike the reactor module 100, the reactor module 400 includes columns of conduits 411a/b/c/d/e (411a is not viewable) and columns of UV light sources 421a/b/c/d that are arranged along a height or third axis of the reactor module 400 and thus are angled or perpendicular to the direction of air flow through the reactor module 400. Additionally, there are multiple columns of UV light sources 421a/b/c/d as opposed to just one row of UV light sources. The arrangement of the conduits 110 and the UV light sources 120 of the reactor module 400 can advantageously enable more contact between the air and the conduits 110, or more particularly the surface of the conduits 110 coated with photocatalytic material, as well as between the air and the UV light. In doing so, the reactor module can provide improved treatment of the incoming air. Additionally, the arrangement of the conduits 110 and the UV light sources 120 of the reactor module 400 can advantageously enable a higher air throughput capacity.

Figure 4B:
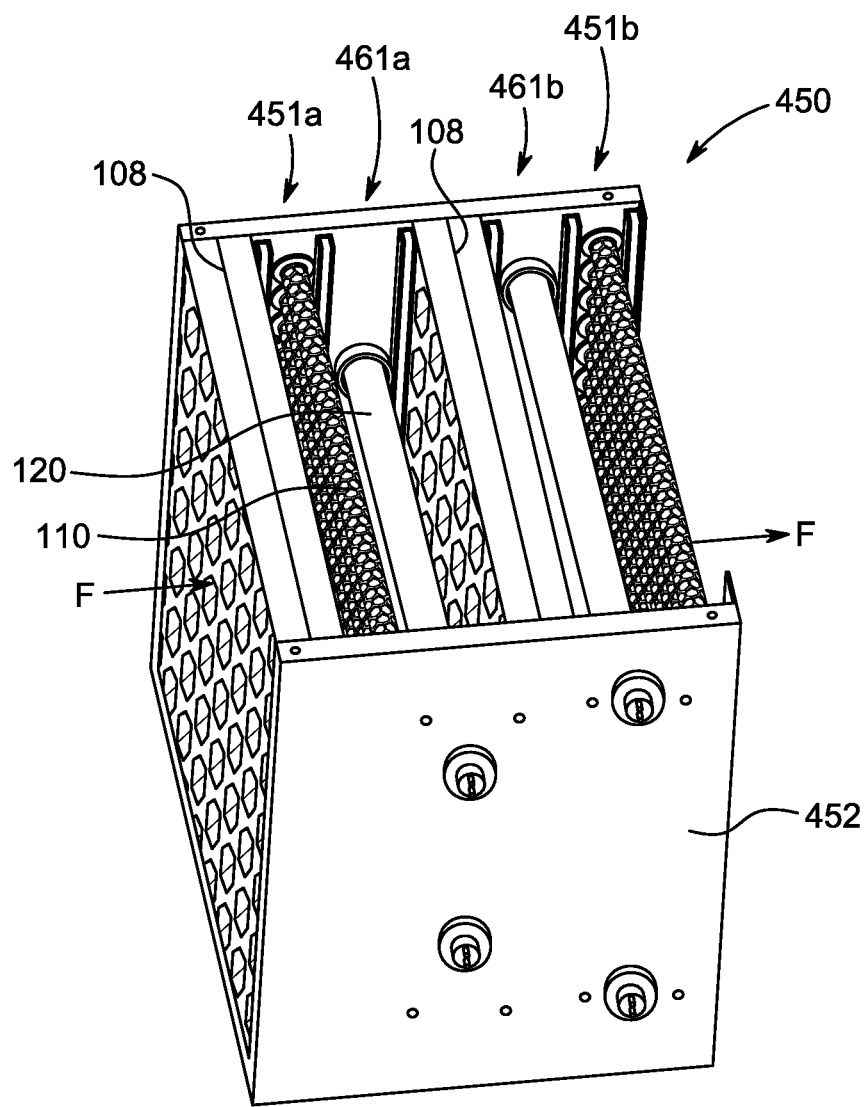

FIG. 4B is a partially schematic view of another reactor module 450, in accordance with embodiments of the present technology. For illustrative purposes, the top sidewall of the housing 452 has been removed from FIG. 4B. The reactor module 450 includes a similar arrangement and many of the same components/features as the reactor module 400 described with reference to FIG. 4A. For example, the reactor module 450 includes the conduits 110 arranged in columns 451a/b, UV light sources 120 arranged in columns 461a/b along a height or third axis of the reactor module 450 and sandwiched between the conduit columns 451a/b, and a first panel member 108 proximal to the first column of conduits 451a. Additionally, the reactor module 450 includes a second panel member 108 disposed between adjacent UV light sources 120 and/or conduits 110. In some embodiments, the reactor module 450 may only include the second panel member 108 and omit the first panel member 108 proximal to the first column of conduits 451a. The second panel member 108 can include all or some of the features of the panel member previously described. For example, the second panel member 108 can comprise aluminum and span an entire height and/or lateral width of the housing 452. Additionally, the second panel member 108 can include a plurality of holes and comprise a photocatalyst material, as described elsewhere herein. Advantageously, the second panel member 108 can promote treatment efficacy of the reactor module 450 and/or sterilization of the air flowing through the reactor module 450, as well as ensure air flow is not concentrated in an intermediate region of the reactor module 450.

Figure 5A:
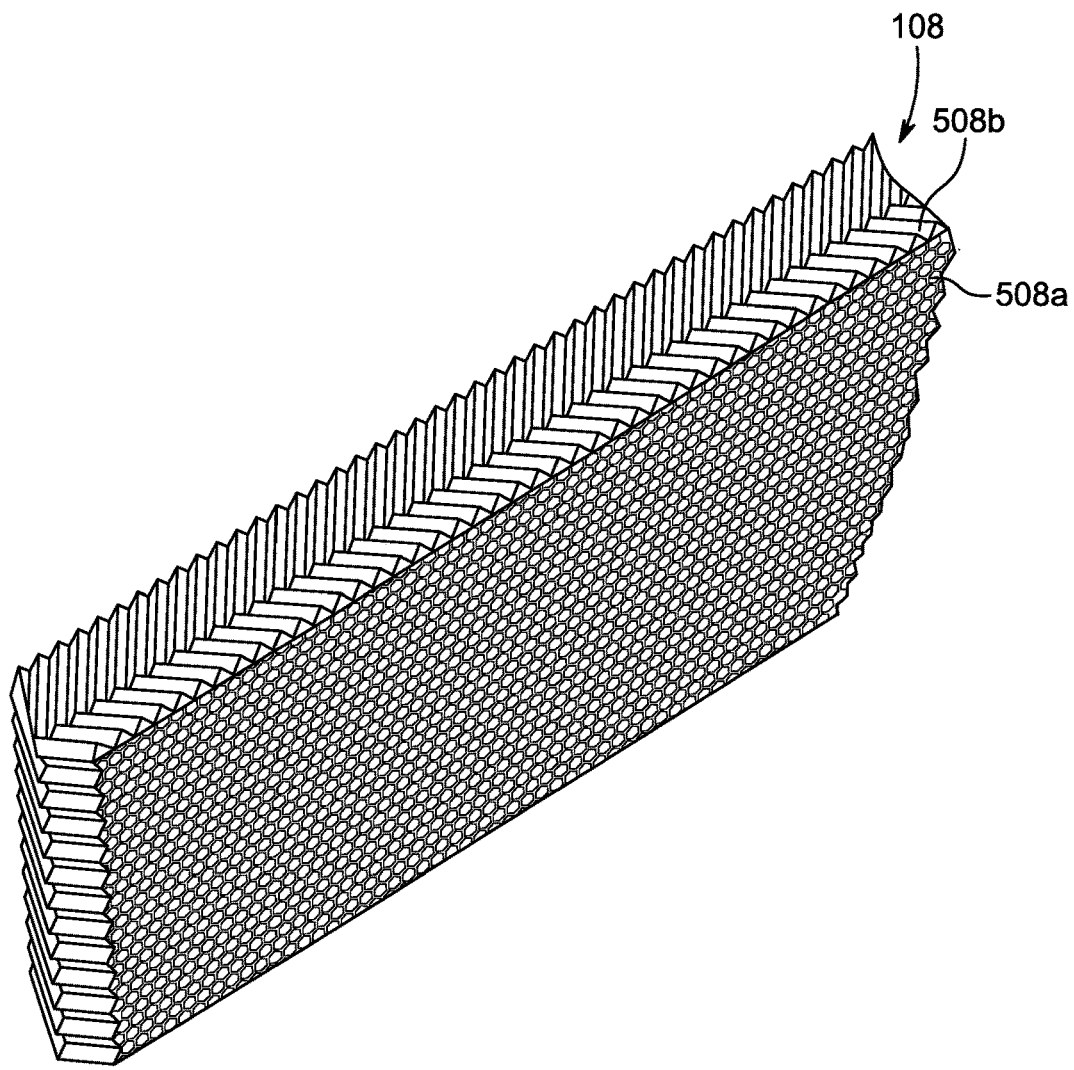
FIGS. 5A and 5B are partially schematic isometric and top views, respectively, of the panel member of the reactor module of FIG. 1A.
Figure 5B:
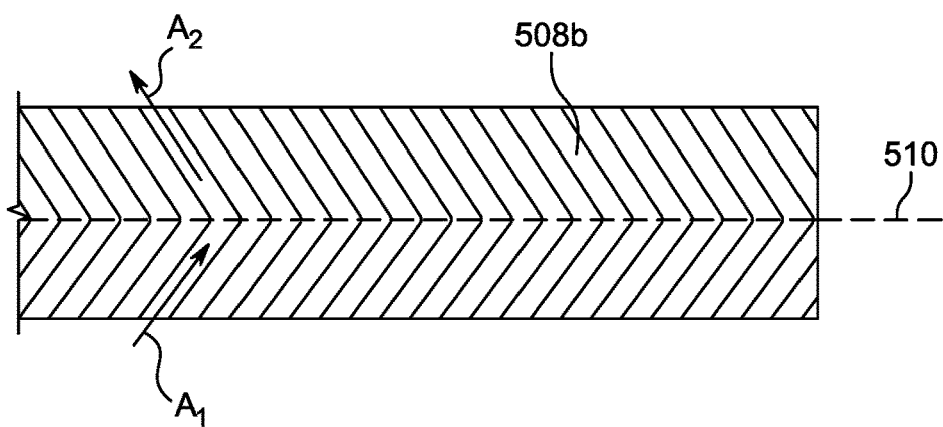

FIGS. 5A and 5B are partially schematic isometric and top views, respectively, of the panel member 108 of the reactor module of FIG. 1A. As previously described, the panel member 108 can include a plurality of holes or openings 109 extending through the panel member 108, each defining paths for air to flow through. Additionally, the panel member 108 and/or the holes 109 of the panel member 108 can comprise a catalyst and/or photocatalytic material, such that air flow through the panel member 108 that contacts the photocatalytic material can be sterilized via reactions between contaminants in the air and the hydroxyl free radicals present on the surface of the panel member 108. As shown in FIG. 5B, the path through the panel member 108 can include a change in direction, e.g., at a midline or intermediate region 510 of the panel member 108. For example, the path through the panel member 108 can include travel in a first direction, as indicated by arrow ($A_1$), and then travel in a second direction, as indicated by arrow ($A_2$), wherein the second direction is different from and angled relative to the first direction. The change in direction can help ensure more contact between the air and the photocatalytic material of the panel member 108. Also, the change in direction can direct UV light toward a side wall of the reactor module and thus limit UV light exposure at the distal outlet end of the reactor module. In some embodiments, the path through the panel member is straight and does not include a change in direction as shown in FIG. 5B.

Figure 6A:
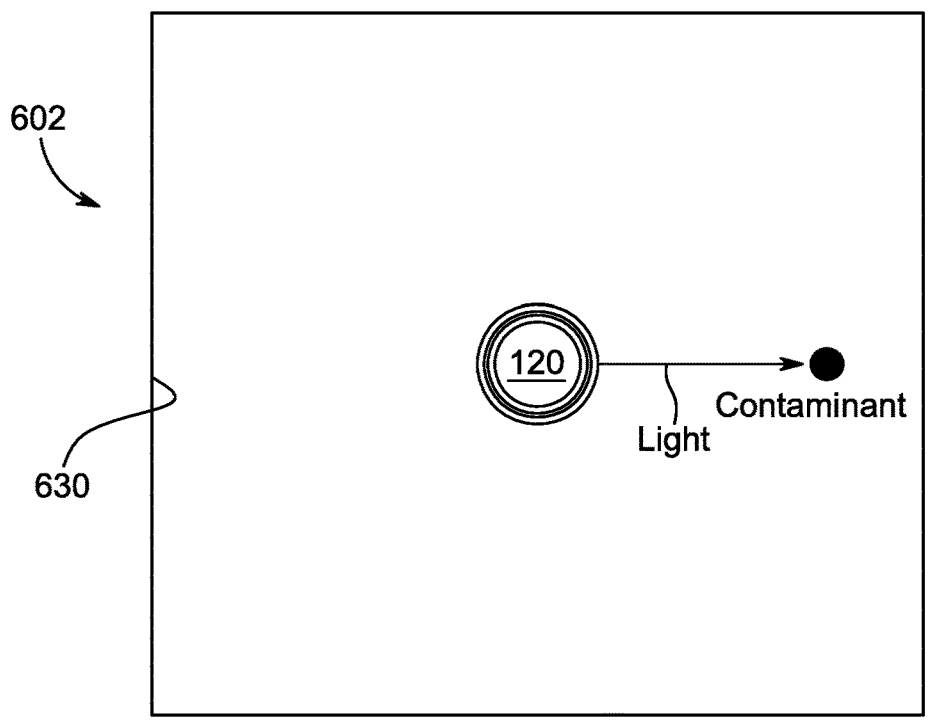
FIG. 6A is a partially schematic view illustrating the path of light emitted in a reactor module that does not include an internal reflective surface.
Figure 6B:
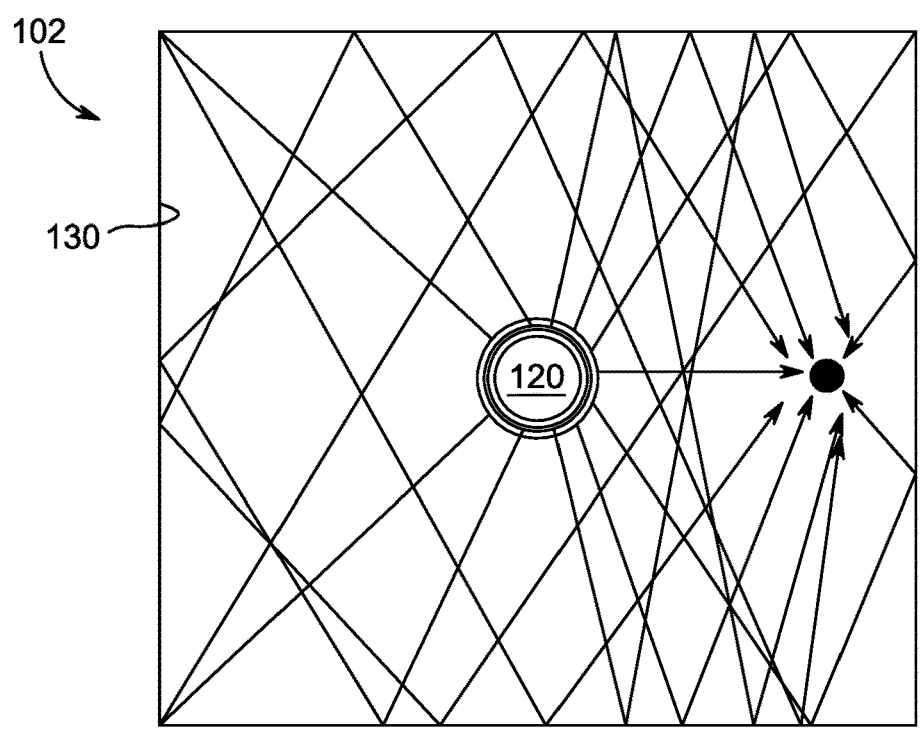
FIG. 6B is a partially schematic view illustrating the path of light emitted in a reactor module that includes an internal reflective surface, in accordance with embodiments of the present technology.

As previously mentioned, the housing (e.g., the housing 102; FIGS. 1A and 1B) of a reactor module can include an interior surface 130 that comprises or is at least partially coated with a reflective material (e.g., chrome or chromium). Such a reflective material can help ensure the light rays emanated from the UV light sources of the reactor module are reflected and maintained within the housing and/or not radiated outside the reactor module. In doing so, the reactor module 100 can more efficiently destroy contaminants in the air, as the likelihood that UV wavelengths emanated from the UV light sources come in contact with and destroy contaminants is significantly increased. FIG. 6A is a partially schematic view illustrating the path of light emitted in a reactor module that does not include an internal reflective surface, and FIG. 6B, in accordance with embodiments of the present technology, is a partially schematic view illustrating the path of light emitted in a reactor module that includes a reflective surface. As shown in FIG. 6A, which assumes that an internal surface 630 of a housing 602 does not include a reflective surface, the only light emitted by the UV light source able to destroy a contaminant is the light emitted directly toward the contaminant. That is, light emitted in any other direction would be absorbed by the internal surface 630 and thus not reflected within the housing. As shown in FIG. 6B, which illustrates the housing 102 and internal reflective surface 130, as described with reference to FIG. 1B, light emitted from the UV light source 120 in any direction is reflected within the housing 102, e.g., until coming in contact with a contaminant. As shown by Reaction 1, the reflective surface 130 of the housing 102 can increase the sterilization rate of the reactor module.

$$S = \exp(-E^*t/Q) \quad \text{(Reaction 1)}$$

wherein:
S=sterilization rate
E=UV strength (mW/cm$^2$)
t=reaction time (seconds)
Q=amount of UV radiation or UV irradiance Each variable of Reaction 1 is improved due to the reflective internal surface 130 of the housing. For example, E (UV strength) and Q (UV irradiance) are each increased via multiple reflections of a UV light. Also, t (reaction time) is increased as contaminants collide with the conduits of the reactor module. Accordingly, the reflectiveness of the internal surface can significantly improve the ability of the reactor module to destroy contaminants in an efficient manner.

Figure 7A:
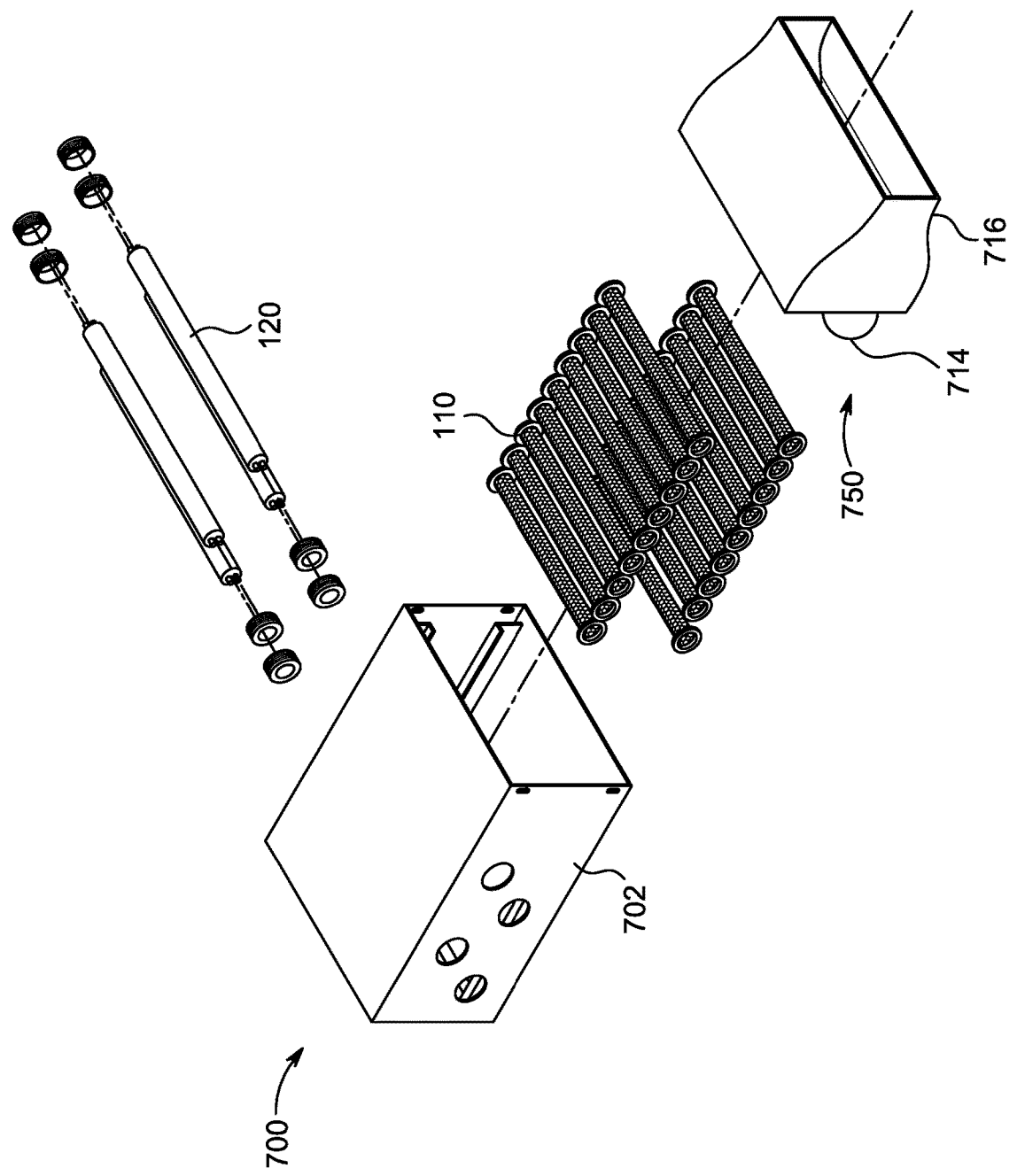
FIG. 7A is a partially schematic isometric view of a wind guide assembly coupled to a reactor module, in accordance with embodiments of the present technology.
Figure 7B:
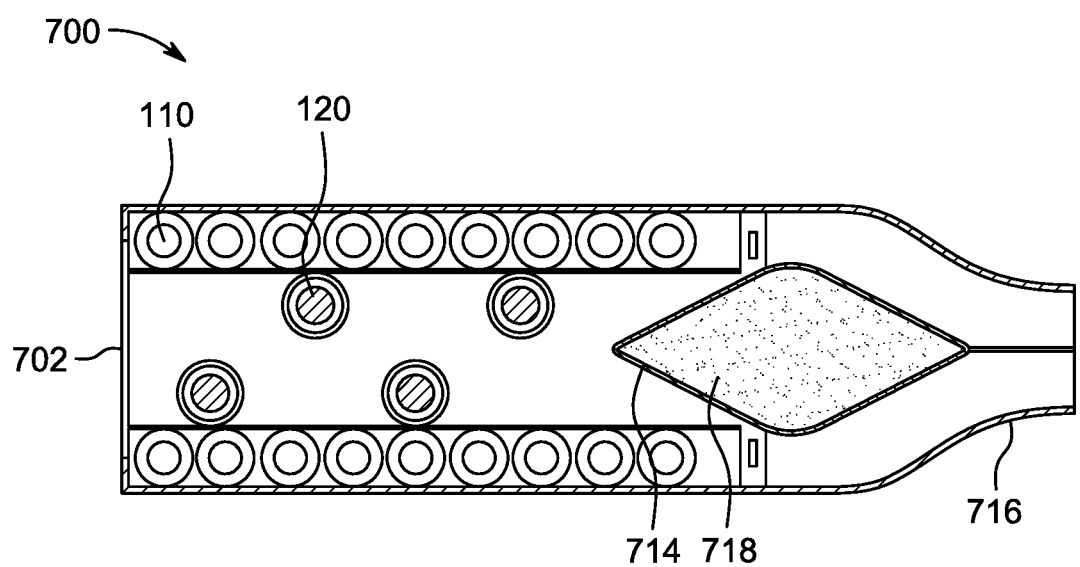
FIG. 7B is a partially schematic side cross-sectional view of the wind guide assembly and reactor module of FIG. 7A.

FIG. 7A is a partially schematic isometric view of a wind guide assembly 750 coupled to a reactor module 700, and FIG. 7B is a partially schematic side cross-sectional view of the wind guide assembly 750 and reactor module of FIG. 7A. Referring to FIGS. 7A and 7B together, the reactor module 700 includes many of the components described with reference to FIGS. 1A and 1B. The wind guide assembly 750 includes a wind guide member and/or silencer 714 positioned downstream of the conduits 110 and/or UV light source 120 of the reactor module 700, and a cover 716 coupled to the housing 102 at or near an outlet of the housing 102. The wind guide member 714 can have an exterior surface that conforms and is complementary to a corresponding abutting interior surface of the cover 716. In some embodiments, the wind guide member 714 is positioned adjacent the cover 716 such that air from the housing 102 is directed and flows between the wind guide member 714 and the interior surface of the cover 716. As shown in FIG. 7B, the wind guide member 714 can include one or more holes or openings 718, and a sound absorbing material capable of absorbing noise and thus at least partially silencing noise resulting from air flow and general operation of the reactor module 100. In some embodiments the wind guide member 714 or portions thereof can be coated with a paint configured to absorb UV light emitted from the UV light source 120, e.g., to ensure UV light is inhibited or prevented from traveling distal to the cover 716 and the user is not exposed to the UV light.

The wind guide member 714 can have a rhombus or other shape that enables the wind guide member 714 to be disposed within an interior portion of the cover 716 and adjacent the conduits 110 and/or UV light sources 120. The rhombus shape can, for example, reduce wind resistance relative to other shapes, and direct the air flow toward the interior ceiling surface of the cover 716. In doing so, the wind guide member 714 and/or the positioning of the wind guide member 714 relative to the cover 716, can enable discharged air flow that is able to travel along ceiling surfaces external to the air treatment device including the reactor module 100, a phenomenon often referred to as the Coanda effect. Stated differently, the discharged treated air stream from the cover 716 can entrain air molecules in the immediately surrounding area and create a low-pressure region, which in turn can stabilize the air stream and allow it flow in a substantially straight line for longer distances under laminar flow conditions. The longer distances traveled for the air flow enable more throughput through the reactor module 100, and thus allow more of the air surrounding the air treatment device including the reactor module 100 to be treated.

The cover 716 can coupled to an outlet portion of the housing 102 and surrounds at least a portion of the wind guide member 714. As such, the cover 716 is configured to receive purified and/or sterilized air that has passed through the housing 702. In some embodiments, the cover 716 can be at least partially coated with a paint configured to absorb UV light from the UV light sources 120. Such paint can ensure UV light is inhibited or prevented from emanating outside the reactor module 100. The cover 716 can have a cross-sectional dimension that decreases in a direction away from the housing 702. Without being bound by theory, decreasing the cross-sectional dimension in such a manner, in combination with other features of the reactor module 100 described elsewhere herein, can aid in (i) decreasing and/or minimizing noise from the reactor module 100 and (ii) increasing the velocity and pressure of the air flow discharged from the cover 716, thereby enabling better circulation of the air flow within the external environment where the treated air is discharged.

Figure 7C:
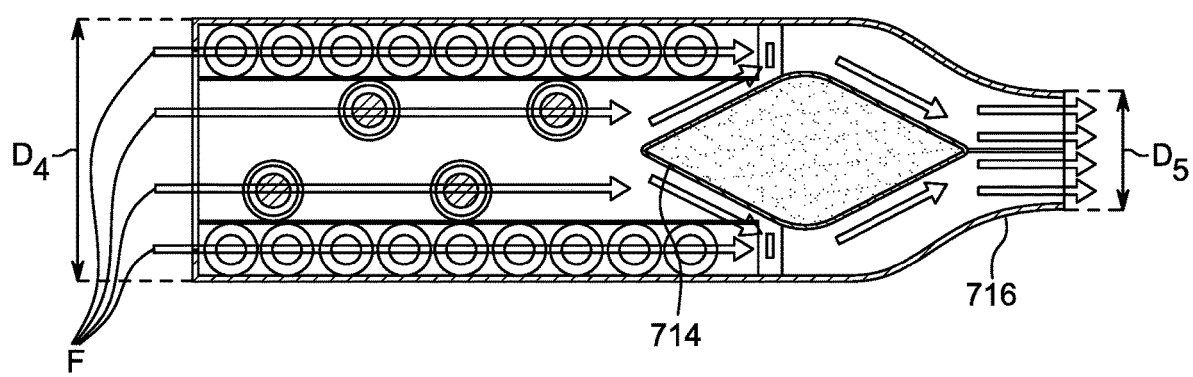
FIG. 7C is a partially schematic cross-sectional view illustrating air flow through the reactor module and wind guide assembly of FIG. 7A, in accordance with embodiments of the present technology.

FIG. 7C is a partially schematic cross-sectional view illustrating air flow through the reactor module of FIG. 7A, in accordance with embodiments of the present technology. As shown in FIG. 7C, air enters the reactor module 100 at an inlet of the housing 702, extending through (i) an intermediate region of the housing vertically between the rows of conduits 110 and where the UV light sources 129 are disposed, and (ii) upper and lower regions of the housing 702 peripheral to the intermediate region where the conduits 110 are disposed. Air flowing through these upper, intermediate, and lower regions are sterilized, e.g., by the combination of the photocatalytic effect of the conduits 110 and the UV light 120. Air flowing through the intermediate regions encounters the wind guide member 714 which guides the air toward the air passing through the upper and lower regions, thereby causing the air flows to mix. The mixed air is then guided toward an outlet at the distal end of the cover 716, which has a distally decreasing cross-sectional dimension. As the air approaches the distal end of the cover 716, the air flow is forced into a smaller cross-sectional area such that the air flow exits the cover 116 as a plurality of parallel air streams exhibiting laminar flow. As also previously described, the discharged treat air from the cover 716 can then entrain air molecules in the immediately surrounding area and create a low pressure region, which in turn can stabilize the air stream and allow it flow in a substantially straight line for longer distances. The longer distances traveled for the air flow enable more throughput through the reactor module 100, and thus allow more of the air surrounding the reactor module 100 to be treated.

Figure 8A:
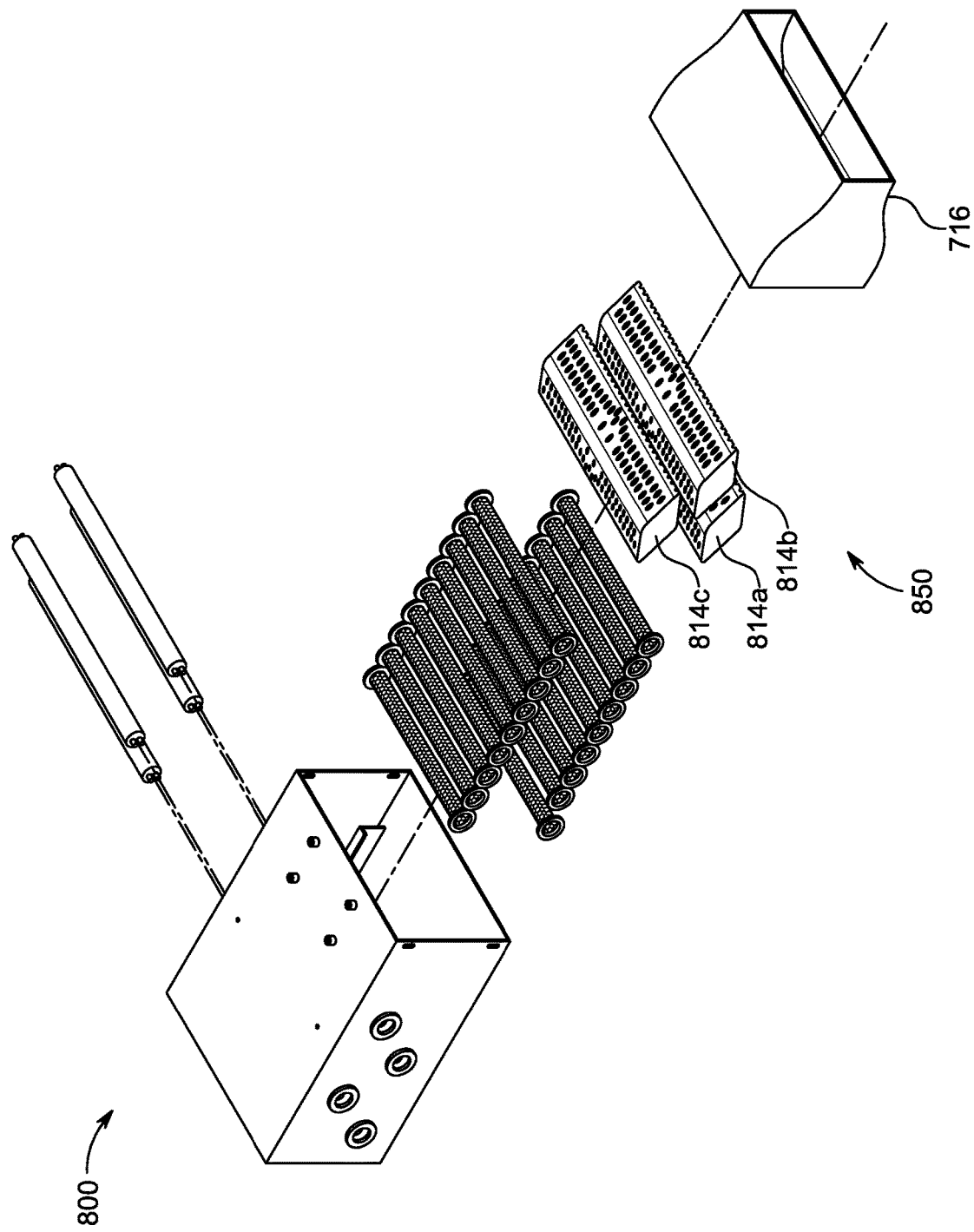
FIG. 8A is a partially schematic cross-sectional view of a wind guide assembly coupled to a reactor module, in accordance with embodiments of the present technology.
Figure 8B:
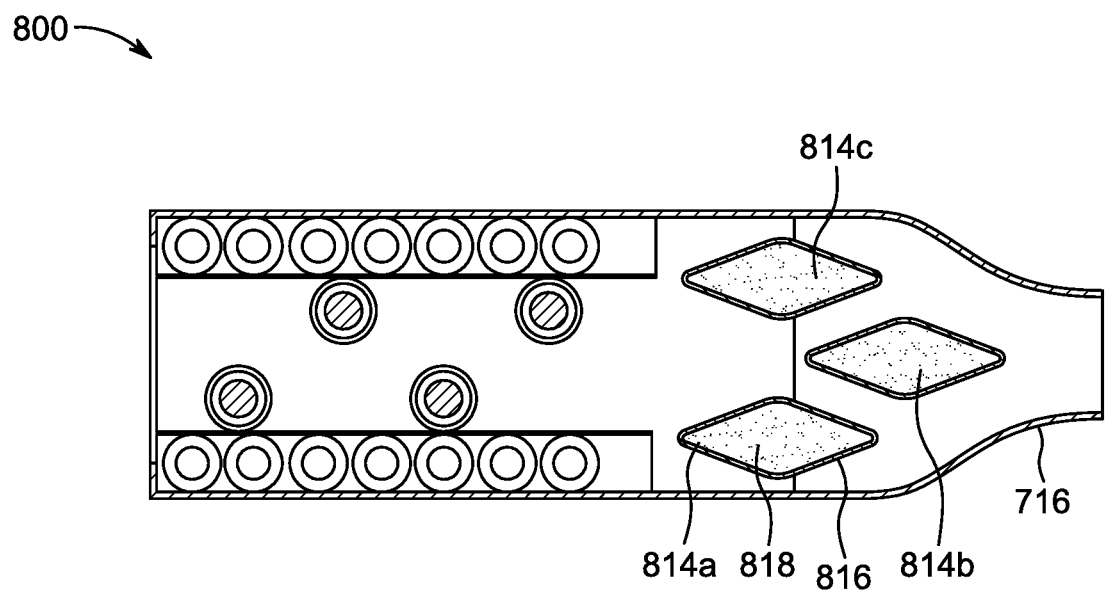
FIG. 8B is a partially schematic side cross-sectional view of the wind guide assembly and reactor module of FIG. 8A.

FIG. 8A is a partially schematic cross-sectional view of a wind guide assembly 850 coupled to the reactor module 800, and FIG. 8B is a partially schematic side cross-sectional view of the wind guide assembly 850 and reactor module of FIG. 8A. The reactor module 800 is generally similar to the reactor module 700 described with reference to FIGS. 7A-7C. The wind guide assembly 850 is similar to the wind guide assembly 750 described with reference to FIGS. 7A-7C, but differs at least in that the single wind guide member 714 is replaced with multiple guide members 814a/b/c (collectively referred to as guide members 814). The guide members 814 can be physically smaller than the guide member 714, but otherwise can have all of the features and functionality of the wind guide member 714. Additionally, the guide member 714 can have all of the features and functionality of the guide members 814. As shown in FIGS. 8A and 8B, the guide members 814 can be arranged adjacent one another to define one or more air channels therebetween. In some embodiments, the guide members 814 can abut one another such that no air channels are formed therebetween and air is forced toward peripheral (e.g., upper and lower) regions of the cover 716. In some embodiments, the guide members 814 can be positioned entirely within the cover 716 downstream of the housing 102. Relative to just a single wind guide member, as shown and described in FIGS. 7A-7C, the guide members 814 of FIGS. 8A and 8B can have an increased overall surface area and thus enable enhanced silencing and noise reduction. As shown in FIGS. 8A and 8B, there are three guide members 814a/b/c coupled to the reactor module 800. However, in other embodiments, more (e.g., 4, 5, 6, etc.) or less guide members 814 may be used.

Figure 9:
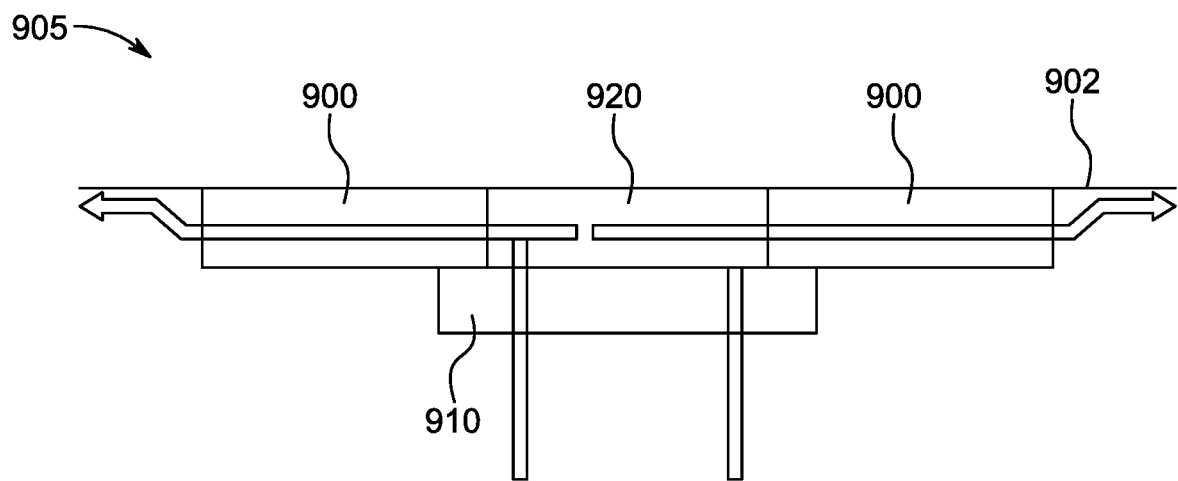
FIG. 9 is a partially schematic cross-sectional side view of an air treatment system including a filter, a fan, and one or more reactor modules, in accordance with embodiments of the present technology.

FIG. 9 is a partially schematic cross-sectional side view of an air treatment system or device 905 including a filter 910, a fan 920, and one or more reactor modules 900, in accordance with embodiments of the present technology. The reactor modules 900 can correspond to the reactor modules 100, 400 or 700, as well as other reactor modules described elsewhere herein. The filter 910 can be configured to receive air from the ambient environment and can filter out a desired particle size depending on the end use or application of the system 905. The filter 910 can include one or more of a high efficiency particulate air (HEPA) filter, a medium filter, a carbon filter, and/or a pretreatment filter, as well as other filters commonly known in the art. The fan 920 can correspond to one or more fans (e.g., two fans, three fans, etc.) and is positioned downstream of the filter 910. The fan 920 can provide the driving force for pulling air through the filter 910 and pushing air toward and through the reactor modules 900.

As shown in FIG. 9, the system 905 can be positioned adjacent or mounted to a ceiling or wall 902. Positioning the system 905 as such can enable discharged air flow to travel along ceiling surfaces external to the air treatment system 905 via the Coanda effect. As previously described, the discharged treated air from the reactor module 900 can entrain air molecules in the immediately surrounding area and create a low-pressure region, which in turn can stabilize the air and allow it flow in a substantially straight line for longer distances under laminar flow conditions. The longer distances traveled for the air flow enable more throughput through the reactor modules 900, and thus allow more of the air surrounding the air treatment system 905 to be treated.

In some embodiments, the filter 910, fan 920, and reactor modules 900 are configured in different arrangements. For example, the fan 920 may be upstream of the reactor module(s) 900, and the reactor module(s) may be upstream of the filter 910. Additionally or alternatively, in some embodiments, the filter 910, fan 920, and reactor modules 900 are arranged in a vertical arrangement, such that air is fed to the system 905 at a base or lower region and treated air is provided from the system 905 at an upper region. For example, the system 905 can comprise a stand, e.g., that is portable and can be easily moved around an indoor environment.

Figure 10A:
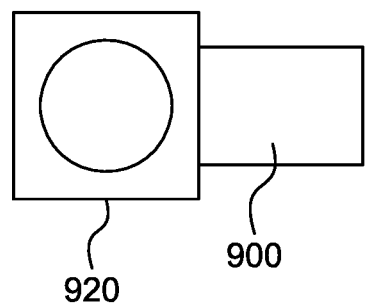
FIGS. 10A-10F are partially schematic top views of various arrangements of a fan and one or more reactor modules, in accordance with embodiments of the present technology.
Figure 10B:
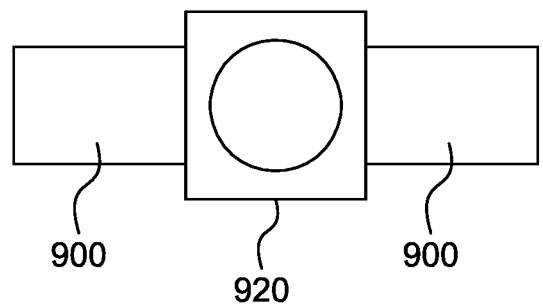
Figure 10C:
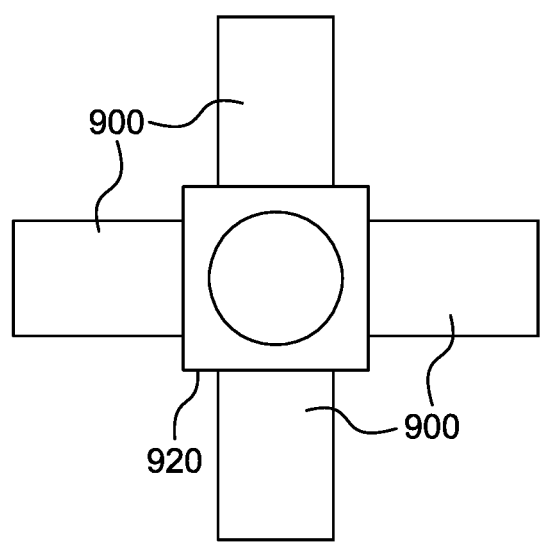
Figure 10D:
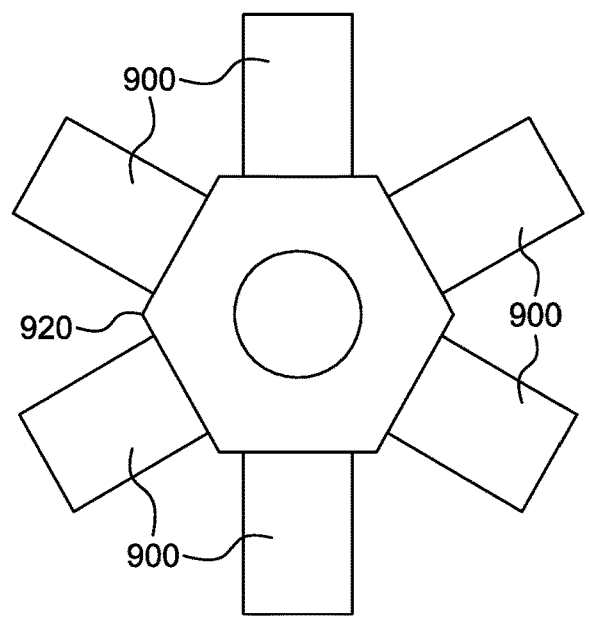
Figure 10E:
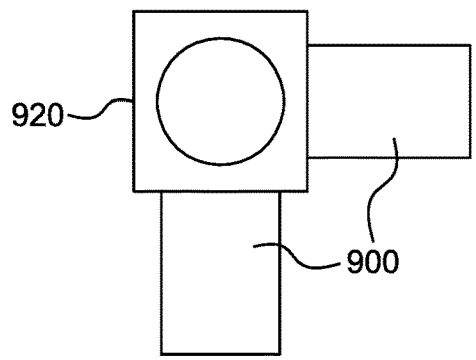
Figure 10F:
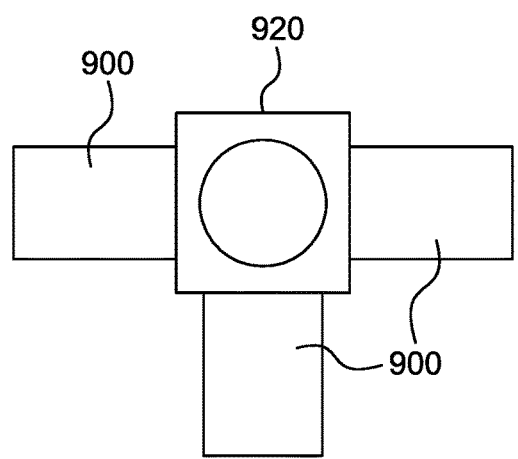

FIGS. 10A-10F are partially schematic views of various arrangements of a fan 920 coupled to one or more of the reactor modules 900, in accordance with embodiments of the present technology. FIG. 10A shows the fan 920 coupled to a single module 900. FIG. 10B shows the fan 920 coupled to two modules 900 extending from the fan 920 in opposite directions (e.g., as shown in FIG. 9). FIG. 10C shows the fan 920 coupled to four modules 900 in which each of the modules are angled approximately 90 degrees relative to adjacent modules. FIG. 10D shows the fan 920 coupled to six modules angled relative to adjacent modules. FIG. 10E shows the fan 920 coupled to two modules 900 angled approximately 90 degrees relative to one another. FIG. 10F shows the fan 920 coupled to three modules 900 angled approximately 90 degrees relative to one another. Depending on the end use or application of the fan 920 and module(s) 900, one or more of FIGS. 10A-10F may be utilized. For example, the configuration of FIG. 10B may optimally be mounted along a straight wall in an elongate room, FIG. 10D may optimally be mounted in the center of a large room, and FIG. 10E may optimally be mounted in the corner of a room. It is worth noting that FIGS. 10A-10F represent but a few examples of possible configurations, as many other configurations are possible and depend upon the desired end use application of the user.

Figure 11:
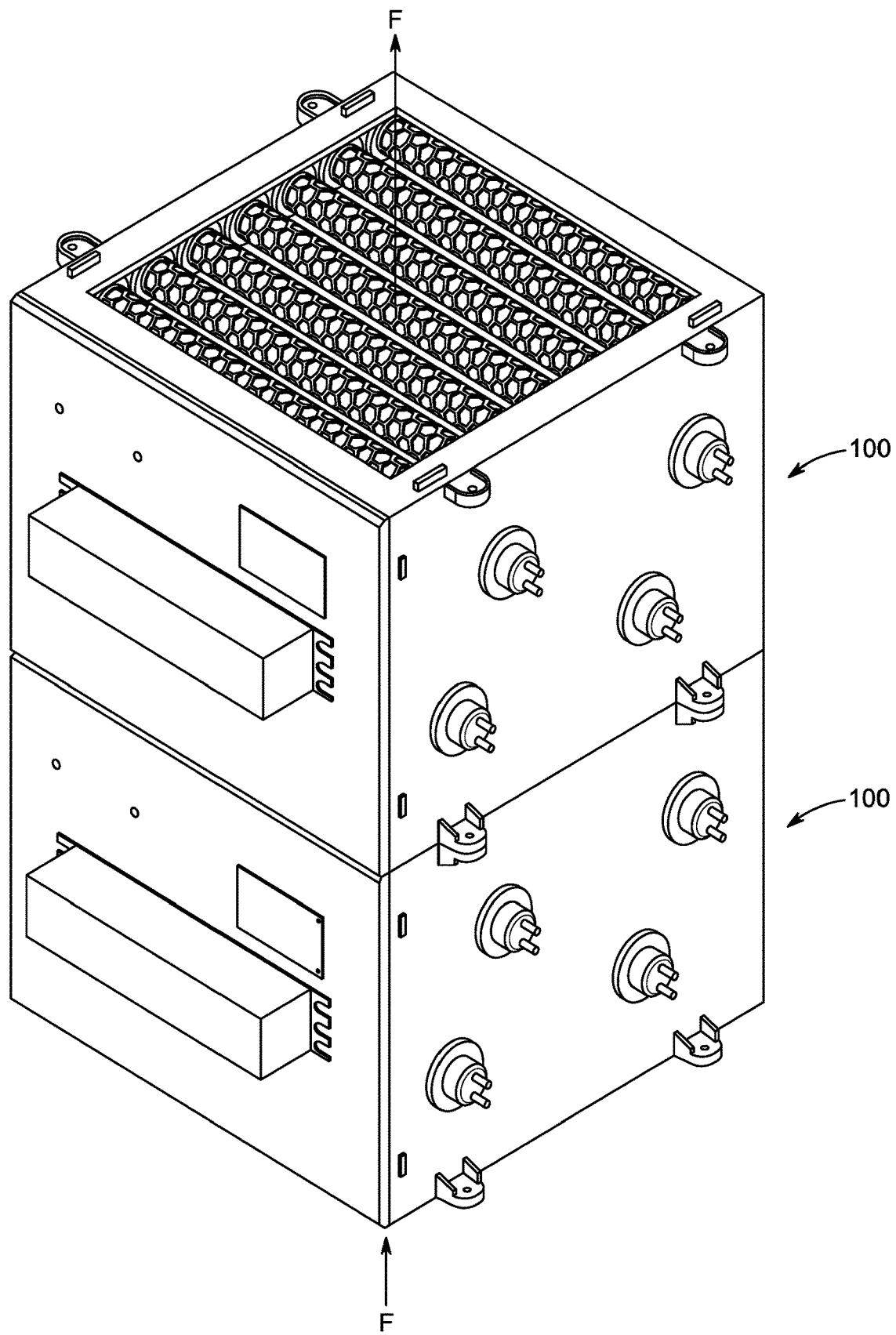
FIG. 11 is a partially schematic isometric view of two stackable reactor modules, in accordance with embodiments of the present technology.

FIG. 11 is a partially schematic isometric view of two stackable reactor modules 100, in accordance with embodiments of the present technology. As shown in FIG. 11, a first reactor module 100 is stacked on top on a second, identical reactor module 100. In the stacked configuration, elements of each of the modules 100 can be aligned to enable them to be secured to one another, e.g., via fasteners (not shown). The ability to couple reactor modules 100 to one another, e.g., in a stackable arrangement, enables increased photocatalytic surface area for the air to contact, which improves reaction time and efficacy of the corresponding air treatment device.

Figure 12A:
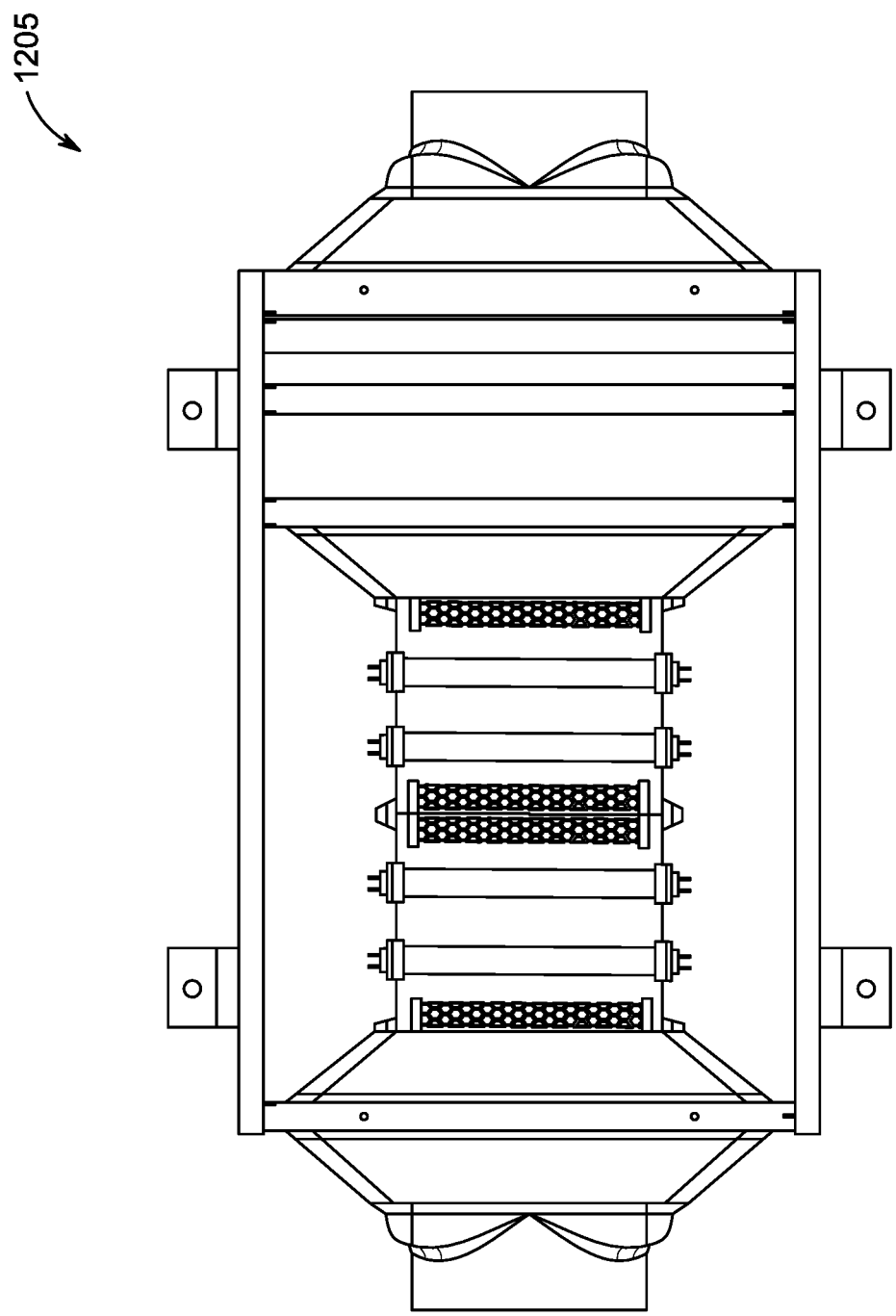
FIG. 12A is a partially schematic side view of an air purification system, in accordance with embodiments of the present technology.
Figure 12B:
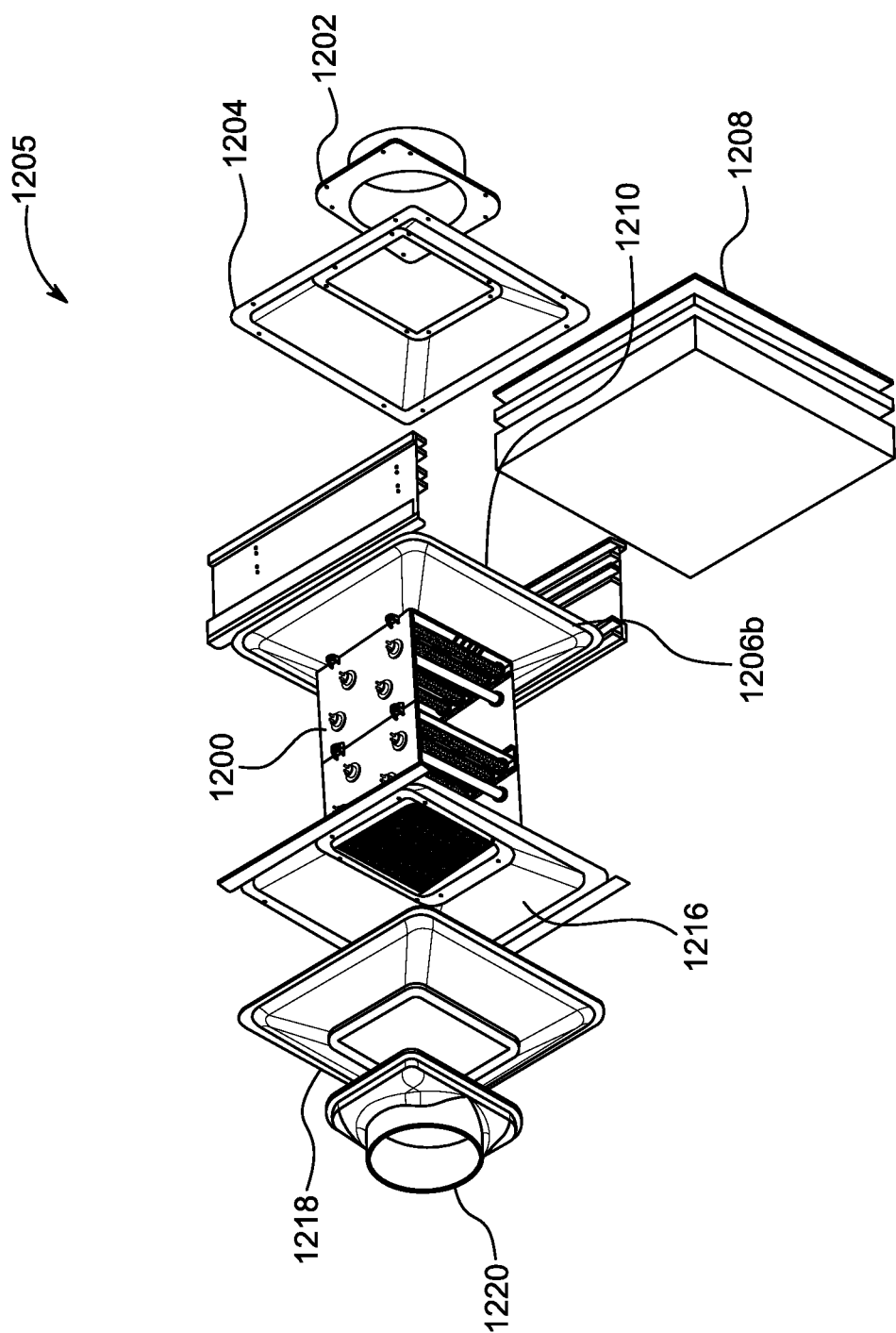
FIG. 12B is a partially schematic exploded view of the air purification system of FIG. 12A.

FIG. 12A is a partially schematic side view of an air sterilization system or device 1205, and FIG. 12B is a partially schematic exploded view of the air sterilization system 1205. For illustrative purposes, the housing of the air sterilization system 1205 has been removed from FIG. 12B. As shown in FIG. 12B, the air sterilization system 1205 includes a first connection port 1202, a first flange 1204 coupled to the first connection port, one or more filters 1208 disposed proximate the filter 1208 (e.g., a HEPA filter, a medium filter, a carbon filter, and/or a pretreatment filter), a casing 1210 at least partially surrounding the filter 1208 and coupled to the first flange 1204, one or more reactor modules 1200 (e.g., the reactor module 100, 400, or 700) having a first end portion coupled to the casing 1210, a second flange 1216 coupled to a second end portion of the reactor modules 1200, a third flange 1218 coupled to the second flange 1216, and a second connection port 1220. The air sterilization system 1205 can be coupled to a fan that can be coupled to either the first port 1202 or the second port 1220. In doing so, air flow through the air sterilization system 1205 can travel from the first port 1202 to the second port 1220, or vice versa from the second port 1220 to the first port 1202.

Figure 13:
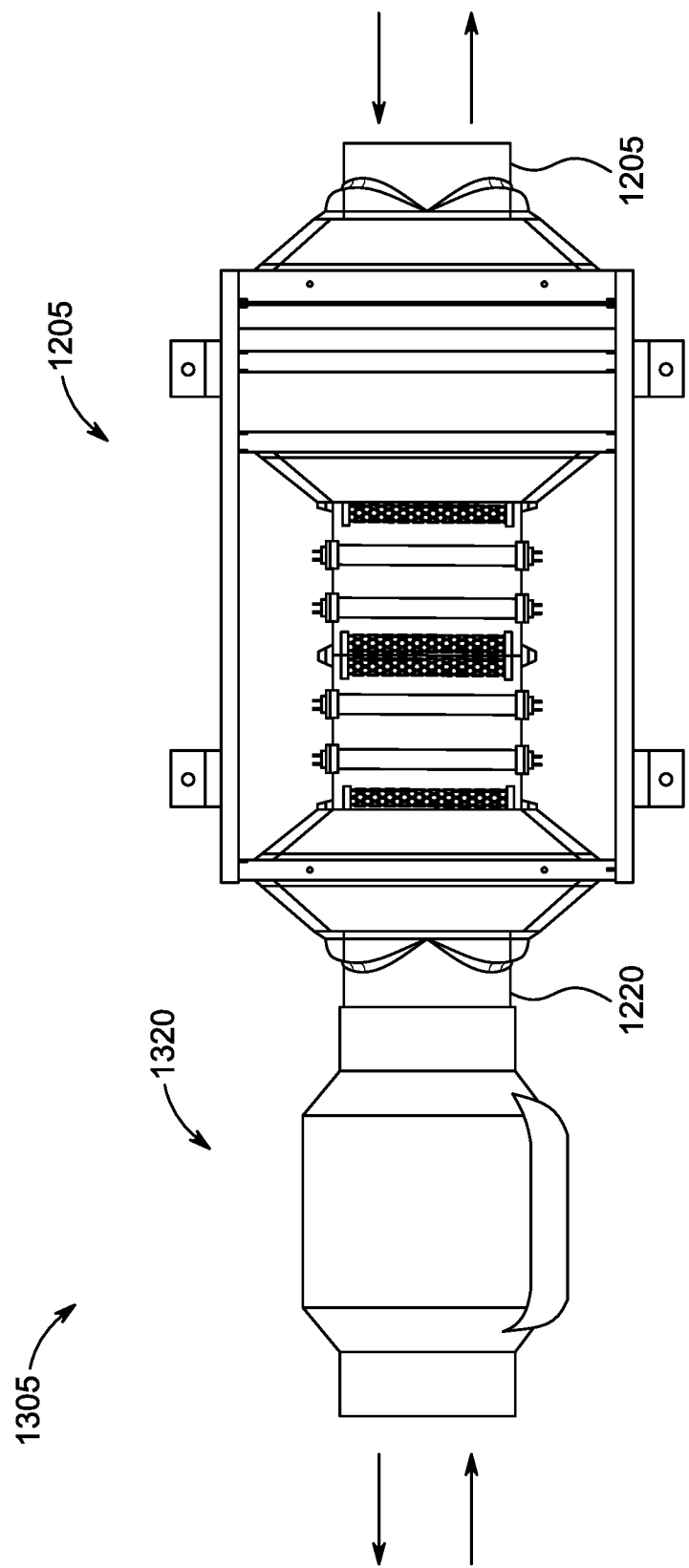
FIG. 13 is a partially schematic side view of the air purification system of FIG. 12A coupled to a fan, in accordance with embodiments of the present technology.

For example, FIG. 13 is a partially schematic side view of an air treatment system or device 1305 including the air sterilization system 1205 of FIG. 12A coupled to a fan 1320. As shown in FIG. 13, the fan 1320 is coupled to the second port 1220. The fan 1320 can be configured to rotate in multiple directions which can dictate the direction of air flow through the air sterilization system 1205. For example, when the fan 1320 rotates in a first direction, air flow is forced through the second port 1220 toward the first port 1205, and when the fan 1320 rotates in a second, opposite direction, air flow is pulled from the first port 1205 toward the second port 1220. In some embodiments, it is preferred to position the fan 1320 at the inlet end of the system 1305, as opposed to the outlet end, such that turbulence of the airflow from the fan 1320 can be mitigated via flow through reactor module(s) 100 and the treated air exiting the system 1305 has a more laminar flow profile.

Figure 14A:
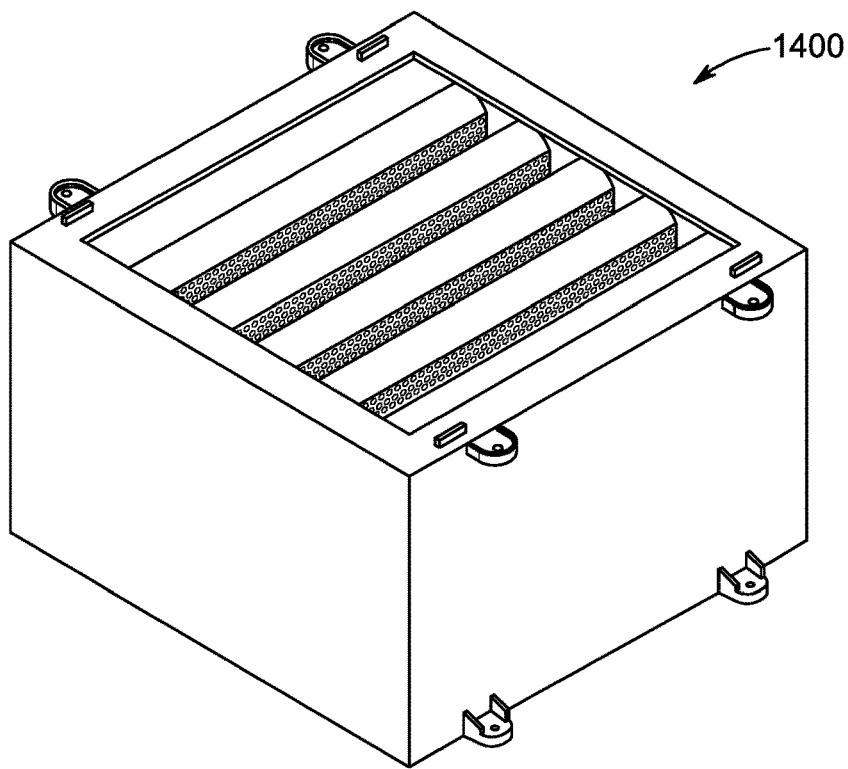
FIG. 14A is a partially schematic isometric view of a treatment module, in accordance with embodiments of the present technology.
Figure 14B:
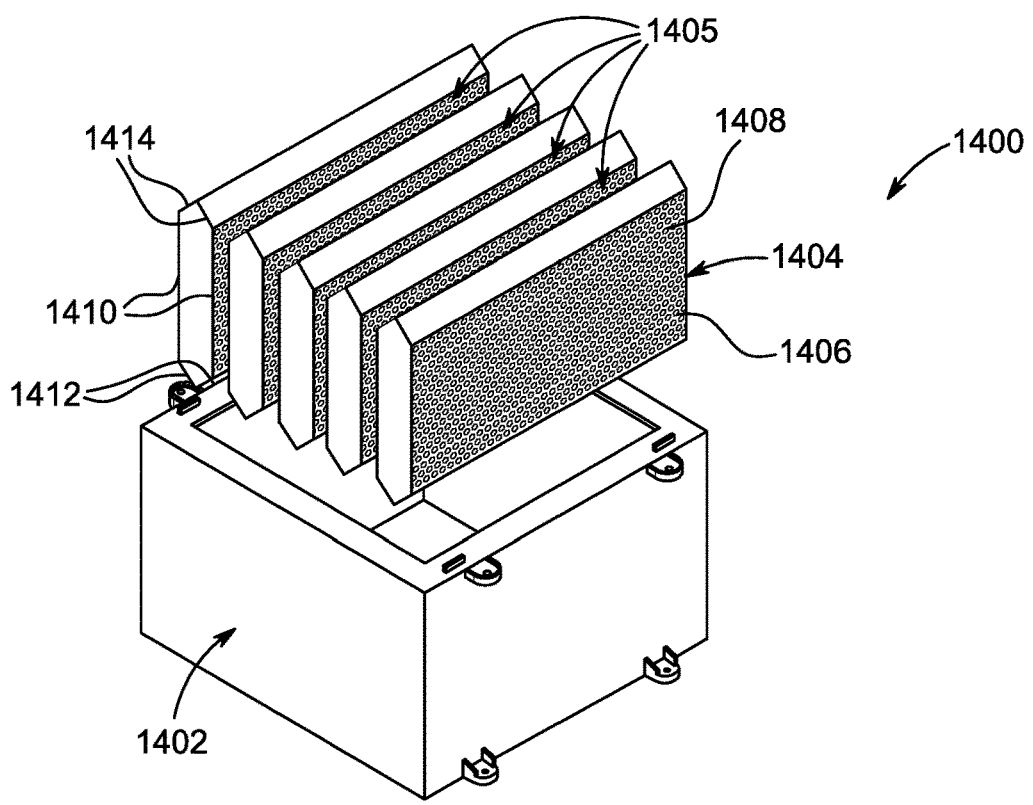
FIG. 14B is a schematic isometric exploded view of the treatment module of FIG. 14A.

FIG. 14A is a partially schematic isometric view of a treatment module 1400, and FIG. 14B is a schematic isometric exploded view of the treatment module 1400. The treatment module 1400 can be coupled to the reactor module 100 described elsewhere herein. In some embodiments, the treatment module 1400 can be stacked on top of the reactor module 100, such that the treatment module 1400 is positioned to receive treated air from the outlet of the reactor module 100 and provide air passing through the treatment module 1400 to the ambient environment. The treatment module 1400 can have conforming structural features that complement corresponding structure features of the reactor module 100 and therein enable the treatment module 1400 to be secured to the reactor module 100.

As shown in FIG. 14B, the treatment module 1400 can include a housing 1402 and a plurality of noise mitigating members 1404 disposed within the housing 1402. The housing 1402 can have a shape similar to that of the reactor module 100 to enable the treatment module 1400 to be coupled or stacked directly on the reactor module 100. The noise mitigating members 1404 can be disposed within the housing 1402 such that adjacent noise members 1404 are spaced apart from one another and therein define channels 1408 to direct air flow received (e.g., from the reactor module 100) through the housing 1402. The channels 1408 can be substantially planar and configured to provide laminar air flow conditions by providing an elongate pathway and/or by decreasing the cross-sectional dimension of the air flow along the direction of airflow. Decreasing the cross-sectional dimension in such a manner can aid in (i) decreasing and/or minimizing noise from the treatment module 1400 and (ii) increasing the velocity and pressure of the air flow discharged from the treatment module 1400, thereby enabling better circulation of the air flow within the external environment where the treated air is discharged.

The noise members 1404 can include one or more holes or openings 1406, and sound absorbing material 1408, e.g., disposed at least partially within the holes 1406. The sound absorbing material 1408 is capable of absorbing and at least partially silencing noise resulting from air flow and general operation of the treatment module 1400. As shown in FIGS. 14A and 14B, the noise members 1404 can be elongate members (e.g., plates) having substantially vertical sidewalls 1410 and inlet and outlet portions that having angled (e.g., outwardly facing) surfaces 1412, 1414. Such surfaces 1412 at the inlet portion can force the incoming air into a smaller cross-section, thereby promoting an increased pressure and the velocity of the air stream. Doing so can stabilize the air stream and allow it flow in a substantially straight line upon exit from the treatment module 1400 for longer distances, e.g., under laminar flow conditions. The longer distances traveled for the air flow can enable more throughput through the modules 100, 1400, and thus allow more of the air surrounding the modules 100, 1400 to be treated (e.g., sterilized and/or purified). As described elsewhere herein, the discharged air flows are able to travel along adjacent surfaces (e.g., ceilings or walls) external to the module 1400 and utilize the Coanda effect. Moreover, the discharged purified and/or sterilized air stream from the treatment module 1400, or corresponding air treatment device, can then entrain air molecules in the immediately surrounding area and create a low pressure region, which in turn can stabilize the air stream and allow it flow in a substantially straight line for longer distances. The longer distances traveled for the air flow enable more throughput through the reactor modules described herein and thus allow more of the ambient air to be treated.

Figure 15:
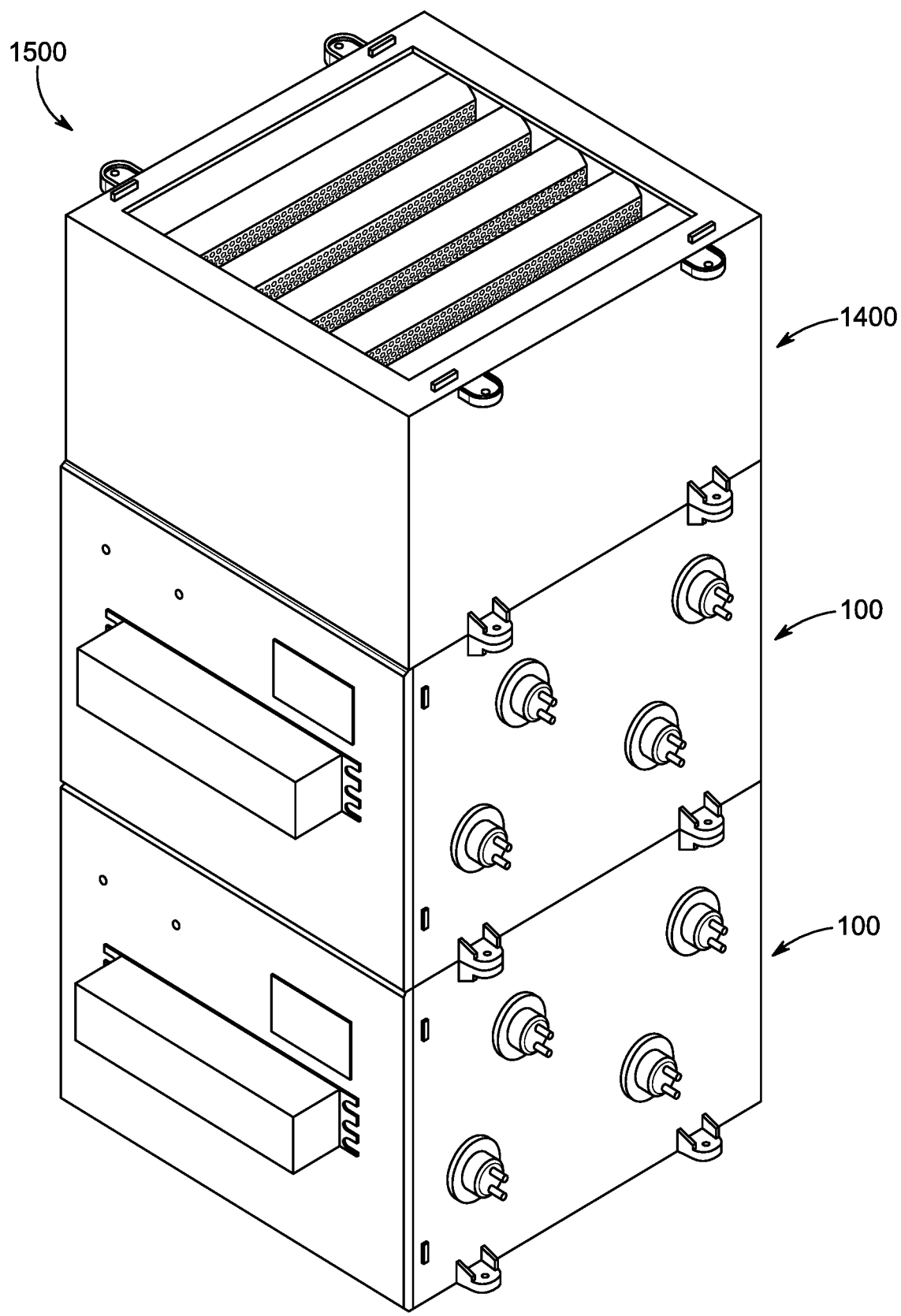
FIG. 15 is a schematic cross-sectional side view of the treatment module of FIG. 14A coupled to the reactor modules of FIG. 8A, in accordance with embodiments of the present technology.

FIG. 15 is a schematic cross-sectional side view of an air sterilization system or device 1500 including the treatment module 1400 coupled to the reactor modules 100, in accordance with embodiments of the present technology. As shown in FIG. 15, the first reactor module 100 is stacked on the second reactor module 100, and the treatment module 1400 is stacked on the second reactor module 100. In the stacked configuration, elements of each of the reactor modules 100 and the treatment module 1400 can be aligned to enable them to be secured to one another, e.g., via fasteners (not shown). As previously described, other embodiments of air treatment system can include more or fewer reactor modules than that shown in FIG. 15.

Figure 16:
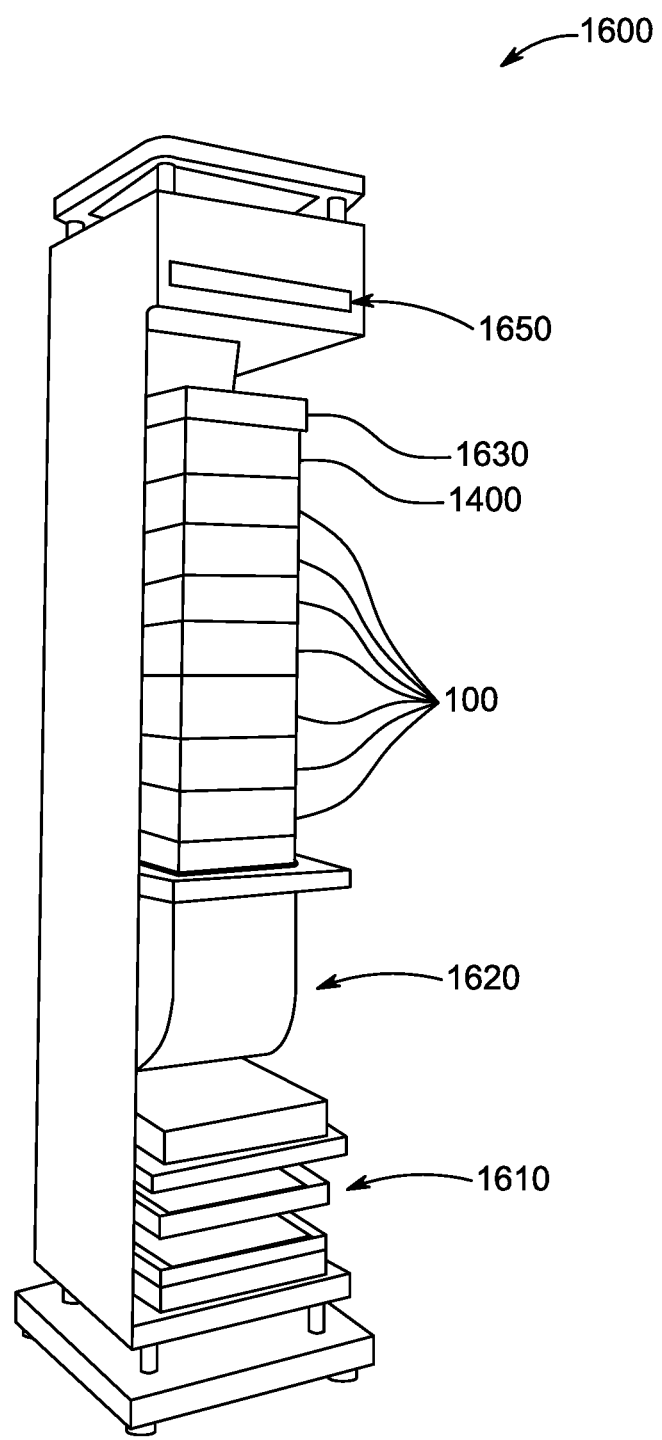
FIG. 16 is a schematic isometric view of an air treatment system, in accordance with embodiments of the present technology.

FIG. 16 is a schematic isometric view of an air treatment system 1600, in accordance with embodiments of the present technology. The treatment system 1600 can be a stand-type treatment system and can include a filter module 1610, a fan or blower 1620, one or more of the reactor modules 100 coupled to and downstream of the fan 1620, the noise module 1400 coupled to and downstream of the reactor modules 100, and a filter 1630 coupled to and downstream of the noise module 1400. The treatment system 1600 can further include a display (e.g., a user interface) and/or controller 1650 for controlling operation of the system 1600 and/or displaying operating conditions and outlet air quality of the system 1600. In some embodiments, the treatment system 1600 can further include other devices and/or components. For example, the treatment system 1600 can include one or more sensors configured to detect impurities and/or dust particles and that are coupled to the controller 1650.

The filter module 1610 can receive untreated air from the ambient environment and can include one or more filters, including a pre-filter, carbon filter, medium filter, and/or HEPA filter. In operation, the filter module 1610 can filter fine dust, bacteria, and/or other contaminants, as described elsewhere herein. The number of filters within the filter module 1610 can be determined based on the quality of the ambient air and allowable pressure drop through the treatment system 1600.

The fan 1620 is positioned downstream of the filter module 1610 and receives filtered air therefrom. The fan 1620 can increase the pressure and/or flow of the air flow received from the filter module 1610. The fan 1620 can correspond to one or more fans (e.g., two fans, three fans, etc.). The fan 1620 is positioned and configured to provide pressurized and filtered air to the one or more reactor modules 100.

As shown in FIG. 16, the treatment system 1600 includes seven reactor modules. However, in other embodiments more or less reactor modules 100 may be included, depending on the desired capacity of the treatment system 1600, with more reactor modules 100 being necessary for a higher capacity of treated air. The reactor modules 100 can be substantially similar or identical to one another, and stackable. The noise module 1400 is positioned to receive treated and/or sterilized air from the most downstream reactor module 100, and to at least partially silence the air stream, e.g., via the noise members 1404 (FIG. 14) as previously described. The filter 1630 is coupled to the noise module 1400 and positioned to receive the at least partially silenced air. The filter 1630 can include a urethane carbon filter, and/or other types of filters depending on a desired application for the treatment system 1600.

III. Conclusion

It will be apparent to those having skill in the art that changes may be made to the details of the above-described embodiments without departing from the underlying principles of the present disclosure. In some cases, well known structures and functions have not been shown or described in detail to avoid unnecessarily obscuring the description of the embodiments of the present technology. Although steps of methods may be presented herein in a particular order, alternative embodiments may perform the steps in a different order. Similarly, certain aspects of the present technology disclosed in the context of particular embodiments can be combined or eliminated in other embodiments. Furthermore, while advantages associated with certain embodiments of the present technology may have been disclosed in the context of those embodiments, other embodiments can also exhibit such advantages, and not all embodiments need necessarily exhibit such advantages or other advantages disclosed herein to fall within the scope of the technology. Accordingly, the disclosure and associated technology can encompass other embodiments not expressly shown or described herein, and the invention is not limited except as by the appended claims.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list can be interpreted as including (a) any single item in the list, (b) all of the items in the list, or (c) any combination of the items in the list. Additionally, the term "comprising," "including," and "having" should be interpreted to mean including at least the recited feature(s) such that any greater number of the same feature and/or additional types of other features are not precluded.

Reference herein to "one embodiment," "an embodiment," "some embodiments" or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

Unless otherwise indicated, all numbers expressing concentrations, dimensions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

The disclosure set forth above is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The present technology is illustrated, for example, according to various examples described below. Various examples of the present technology are described as numbered clauses (1, 2, 3, etc.) for convenience. These are provided as examples and do not limit the present technology. It is noted that any of the dependent clauses may be combined in any combination, and placed into a respective independent clause 1. A reactor module configured to treat air, the reactor module comprising:
   a housing having an inner surface, an inlet, an outlet opposite the inlet, a length dimension defining a first axis extending from the inlet to the outlet, and a width dimension defining a second axis perpendicular to the first axis;
   an ultraviolet (UV) light source disposed within the housing, the UV light source extending in a lateral direction parallel to the second axis; and
   a plurality of hollow elongate conduits disposed within the housing and peripheral to the UV light source, individual conduits extending in the lateral direction parallel to the second axis and including a plurality of holes,
   wherein the inner surface of the housing comprises a reflective material such that, in operation, UV light emitted from the UV light source is reflected internally within the housing.

2. The reactor module of any one of the clauses herein, wherein the reflective surface comprises chrome or chromium.

3. The reactor module of any one of the clauses herein, wherein the conduits are coated with a solution comprising titanium dioxide.

4. The reactor module of clause 3, wherein the solution comprises between 2-4% by weight titanium dioxide.

5. The reactor module of any one of the clauses herein, wherein the individual conduits are cylindrical and are made from a non-metal material, and wherein an outer surface of the conduits comprising a plurality of holes.

6. The reactor module of clause 5, wherein the holes have a hexagonal shape, and wherein a maximum dimension of any one of individual holes is no more than 10 millimeters (mm) and the individual holes are spaced apart from neighboring individual holes by no more than 4 mm.

7. The reactor module of any one of the clauses herein, further comprising a panel member that extends along an entire height dimension and width dimension of the housing and is disposed along the first axis proximal to the conduits, wherein at least a portion of the panel member is coated with a photocatalytic material.

8. The reactor module of clause 7, wherein the panel member includes a plurality of openings defining corresponding channels configured to receive untreated air from the inlet of the housing, wherein the channels include a first portion extending in a first direction extending toward the outlet and a second portion extending from and distal to the first portion, the second portion extending in a second direction toward the outlet and being angled relative to the first direction.

9. The reactor module of any one of the clauses herein, wherein the conduits include a first set of conduits arranged in a row on a first side of the UV light sources and a second set of conduits arranged in a row on a second side of the UV light source opposite the first side, the first set of conduits and the second set of conduits being disposed within the housing along the first axis.

10. The reactor module of any one of the clauses herein, wherein:
   the UV light source includes a first set of UV light sources arranged in a first UV column and a second set of UV light sources arranged in a second UV column,
   the conduits include a first set of conduits arranged in a first conduit column proximal to the first UV column, a second set of conduits distal to the first UV column and proximal to the second UV column, and a third set of conduits distal to the second UV column, and
   the first UV column, the second UV column, the first conduit column, the second conduit column, and the third conduit column are each disposed within the housing along a third axis perpendicular to the first axis and the second axis.

11. The reactor module of any one of the clauses herein, wherein the UV light source includes at least (i) a first UV light source, (ii) a second UV light source distal to the first UV light source and vertically offset from the first UV light source, and (iii) a third UV light source distal to the second UV light source and vertically offset from the second UV light source.

12. The reactor module of any one of the clauses herein, wherein the UV light source is configured to emit at least one of UVB wavelengths of 280-315 nanometers (nm) or UVC wavelengths of 100-280 nm.

13. The reactor module of any one of the clauses herein, wherein the housing includes opposing sidewalls having (i) holes configured to receive the UV light source and (ii) holders configured to receive end portions of the conduits, the holders being peripheral to holes on the sidewalls 14. The reactor module of any one of the clauses herein, wherein the length dimension of the housing is smaller than the width dimension of the housing.

15. An air treatment device, comprising:
   one or more reactor modules, wherein individual reactor modules comprise—
      a housing having an inner surface, an inlet, an outlet opposite the inlet, a length dimension defining a first axis extending from the inlet to the outlet, and a width dimension defining a second axis perpendicular to the first axis;
      an ultraviolet (UV) light source disposed within the housing, the UV light source extending in a lateral direction parallel to the second axis; and
      a plurality of hollow elongate conduits disposed within the housing and peripheral to the UV light source, individual conduits extending in the lateral direction parallel to the second axis and including a plurality of holes,
      wherein the inner surface of the housing comprises a reflective material such that, in operation, UV light emitted from the UV light source is reflected internally within the housing,
   a fan in fluid communication with the reactor module; and
   a filter in fluid communication with the reactor module.

16. The air treatment device of any one of the clauses herein, further comprising a panel member that extends along an entire height dimension and width dimension of the housing and is disposed along the first axis proximal to the conduits, wherein at least a portion of the panel member is coated with a photocatalytic material.

17. The air treatment device of any one of the clauses herein, wherein the one or more reactor modules includes a first reactor module, and a second reactor module stackable on the first reactor module.

18. The air treatment device of any one of the clauses herein, further comprising a treatment module distal to the one or more reactor modules and positioned to receive air therefrom, the treatment module including a housing, a plurality of noise mitigating members disposed within the treatment module housing and spaced apart from one another to define elongate channels, wherein the channels are configured to direct the air from an inlet of the treatment module to an outlet of the treatment module.

19. The air treatment device of any one of the clauses herein, wherein the reactor module housing and the treatment module housing each has the same square or rectangular shape.

20. The air treatment device of any one of the clauses herein, wherein the reactor modules include at least two reactor modules stacked on top of one another, the treatment module being stacked on top of an outermost one of the three reactor modules.

21. The air treatment device of any one of the clauses herein, wherein the noise mitigating members each comprises a plurality of holes, and a sound absorbing material disposed within at least some of the holes, the noise mitigating members being configured to reduce sound output from the air treatment device.

22. The air treatment device of any one of the clauses herein, wherein the noise mitigating members and the channels extend along the first axis, and wherein individual channels include an inlet region having a first cross-sectional dimension and an intermediate region downstream of the inlet region having a second cross-sectional dimension smaller than the first cross-sectional dimension.

23. The air treatment device of any one of the clauses herein, wherein:
the fan is upstream of the one or more reactor modules; and
the filter is downstream of the one or more reactor modules, the filter including one or more of a high efficiency particulate air (HEPA) filter, a medium filter, a carbon filter, and/or a pretreatment filter.

24. The air treatment device of any one of the clauses herein, further comprising a wind guide assembly distal to the one or more reactor modules and positioned to receive air therefrom, the wind guide assembly including a cover, and a guide member disposed at least partially within and proximal to the cover.

25. The air treatment device of clause 24, wherein the cover includes a cross-sectional dimension that decreases in a distal direction.

26. A reactor module configured to treat air flowing therethrough, the reactor module comprising:
a housing having an inlet at a first end, an outlet at a second end opposite the first end, and sidewalls extending from the inlet to the outlet along a first axis, the housing having a first dimension along the first axis and a second dimension along a second axis perpendicular to the first axis, wherein the second dimension is longer than the first dimension;
an ultraviolet (UV) light source disposed within the housing, the UV light source extending between opposing ones of the sidewalls and in a direction parallel to the second axis; and
a plurality of hollow elongate conduits disposed within the housing and extending between the opposing sidewalls, wherein the individual conduits (i) are radially outward of the UV light source, (ii) extend in a direction parallel to the second axis, and (iii) include a plurality of holes each having a polygon shape.

27. The reactor module of any one of the clauses herein, wherein the housing has an inner surface comprising a reflective material such that, in operation, UV light emitted from the UV light source is reflected internally within the housing.

28. The reactor module of any one of the clauses herein, wherein the housing has an inner surface comprising a reflective material comprising chrome or chromium, and wherein the UV light source is configured to emit at least one of UVB wavelengths of 280-315 nanometers (nm) or UVC wavelengths of 100-280 nm.

29. The reactor module of any one of the clauses herein, wherein the conduits are coated with a solution comprising between 2-4% by weight titanium dioxide, the titanium dioxide including no more than 80% by weight anatase titanium dioxide and a balance of rutile titanium dioxide.

30. The reactor module of any one of the clauses herein, wherein the holes of the individual conduits have a hexagonal shape, and wherein the conduits comprise a plastic material.

31. A method of treating conduits to be used in an air treatment device, the method comprising:
washing the conduits using ultrasonic waves;
drying the washed conduits at a first predetermined temperature for a first predetermined amount of time;
applying a photocatalyst to the conduits; and
after applying the photocatalyst, drying the conduits at a second predetermined temperature for a second predetermined amount of time.

32. The method of any one of the clauses herein, wherein applying the photocatalyst comprising spray coating or dip coating the photocatalyst.

33. The method of any one of the clauses herein, further comprising, prior to drying the conduits at the second predetermined temperature and after applying the photocatalyst, measuring coating parameters of the conduits.

34. The method of any one of the clauses herein, further comprising, prior to applying the photocatalyst, measuring a contact angle associated with a surface tension of the conduits.

35. The method of any one of the clauses herein, further comprising, prior to drying the washed conduits, washing the washed conduits a second time using ultrasonic waves.

I claim:

1. A reactor module configured to treat air, the reactor module comprising:
a housing having an inner surface, an inlet, an outlet opposite the inlet, a length dimension defining a first axis extending from the inlet to the outlet, and a width dimension defining a second axis perpendicular to the first axis, wherein, in operation, air flowing through the housing passes from the inlet and toward the outlet along the first axis;
an ultraviolet (UV) light source disposed within the housing, the UV light source extending in a lateral direction parallel to the second axis; and
a plurality of hollow elongate conduits disposed within the housing and peripheral to the UV light source, the conduits including a first set of conduits arranged on a first side of the UV light source and a second set of conduits arranged on a second side of the UV light source opposite the first side, individual conduits extending in the lateral direction parallel to the second axis,
wherein the inner surface of the housing comprises a reflective material such that, in operation, UV light emitted from the UV light source is reflected internally within the housing.

2. The reactor module of claim 1, wherein the reflective surface comprises chrome or chromium.

3. The reactor module of claim 1, wherein the conduits are coated with a solution comprising titanium dioxide.

4. The reactor module of claim 3, wherein the solution comprises between 2-4% by weight titanium dioxide.

5. The reactor module of claim 1, wherein the individual conduits are cylindrical and are made from a non-metal material, and wherein an outer surface of the conduits comprises a plurality of holes.

6. The reactor module of claim 5, wherein the holes have a hexagonal shape, and wherein a maximum dimension of any one of individual holes is no more than 10 millimeters (mm) and the individual holes are spaced apart from neighboring individual holes by no more than 6 mm.

7. The reactor module of claim 1, further comprising a panel member that extends along an entire height dimension and the width dimension of the housing and is disposed along the first axis proximal to the conduits, wherein at least a portion of the panel member is coated with a photocatalytic material.

8. The reactor module of claim 7, wherein the panel member includes a plurality of openings defining corresponding channels configured to receive the air from the inlet of the housing, wherein the channels include a first portion extending in a first direction and a second portion extending from and distal to the first portion, the second portion extending in a second direction angled relative to the first direction.

9. The reactor module of claim 1, wherein the first set of conduits and the second set of conduits are disposed within the housing along the first axis.

10. The reactor module of claim 1, wherein:
the UV light source includes a first set of UV light sources arranged in a first UV column and a second set of UV light sources arranged in a second UV column,
the first set of conduits is arranged in a first conduit column proximal to the first UV column,
the second set of conduits is distal to the first UV column and proximal to the second UV column,
the conduits include a third set of conduits distal to the second UV column, and
the first UV column, the second UV column, the first conduit column, the second conduit column, and the third conduit column are each disposed within the housing along a third axis perpendicular to the first axis and the second axis.

11. The reactor module of claim 1, wherein the UV light source includes at least (i) a first UV light source, (ii) a second UV light source distal to the first UV light source and vertically offset from the first UV light source, and (iii) a third UV light source distal to the second UV light source and vertically offset from the second UV light source.

12. The reactor module of claim 1, wherein the UV light source is configured to emit at least one of UVB wavelengths of 280-315 nanometers (nm) or UVC wavelengths of 100-280 nm.

13. A reactor module configured to treat air, the reactor module comprising:
a housing having an inner surface, an inlet, an outlet opposite the inlet, a length dimension defining a first axis extending from the inlet to the outlet, and a width dimension defining a second axis perpendicular to the first axis, wherein, in operation, air flowing through the housing passes from the inlet and toward the outlet along the first axis;
an ultraviolet (UV) light source disposed within the housing, the UV light source extending in a lateral direction parallel to the second axis; and
a plurality of hollow elongate conduits disposed within the housing and peripheral to the UV light source, individual conduits extending in the lateral direction parallel to the second axis,
wherein the inner surface of the housing comprises a reflective material such that, in operation, UV light emitted from the UV light source is reflected internally within the housing, and
wherein the housing includes opposing sidewalls having (i) holes configured to receive the UV light source and (ii) holders configured to receive end portions of the conduits, the holders being peripheral to holes on the sidewalls.

14. The reactor module of claim 1, wherein the length dimension of the housing is smaller than the width dimension of the housing.

15. An air treatment device, comprising:
one or more reactor modules, wherein individual reactor modules comprise—
a housing having an inner surface, an inlet, an outlet opposite the inlet, a length dimension defining a first axis extending from the inlet to the outlet, and a width dimension defining a second axis perpendicular to the first axis;
an ultraviolet (UV) light source disposed within the housing, the UV light source extending in a lateral direction parallel to the second axis; and
a plurality of hollow elongate conduits disposed within the housing and peripheral to the UV light source, the conduits including a first set of conduits arranged on a first side of the UV light source and a second set of conduits arranged on a second side of the UV light source opposite the first side, individual conduits extending in the lateral direction parallel to the second axis and including a plurality of holes,
wherein the inner surface of the housing comprises a reflective material such that, in operation, UV light emitted from the UV light source is reflected internally within the housing;
a fan in fluid communication with the one or more reactor modules; and
a filter in fluid communication with the one or more reactor modules.

16. The air treatment device of claim 15, further comprising a panel member that extends along an entire height dimension and the width dimension of the housing and is disposed along the first axis proximal to the conduits, wherein at least a portion of the panel member is coated with a photocatalytic material.

17. The air treatment device of claim 15, wherein the one or more reactor modules includes a first reactor module, and a second reactor module stackable on the first reactor module.

18. The air treatment device of claim 15, further comprising a treatment module distal to the one or more reactor modules and positioned to receive air therefrom, the treatment module including a housing, and a plurality of noise-mitigating members disposed within the treatment module housing and spaced apart from one another to define elongate channels, wherein the channels are configured to direct air from an inlet of the treatment module to an outlet of the treatment module.

19. The air treatment device of claim 18, wherein the reactor module housing and the treatment module housing each has the same square or rectangular shape.

20. The air treatment device of claim 18, wherein the reactor modules include at least two reactor modules stacked on top of one another, the treatment module being stacked on top of an outermost one of the two reactor modules.

21. The air treatment device of claim 18, wherein the noise-mitigating members each comprises a plurality of holes, and a sound absorbing material disposed within at least some of the holes, the noise mitigating members being configured to reduce sound output from the air treatment device.

22. The air treatment device of claim 18, wherein the noise-mitigating members and the channels extend along the first axis, and wherein individual channels include an inlet region having a first cross-sectional dimension and an intermediate region downstream of the inlet region having a second cross-sectional dimension smaller than the first cross-sectional dimension.

23. The air treatment device of claim 15, wherein:
the fan is upstream of the one or more reactor modules; and
the filter is downstream of the one or more reactor modules, the filter including one or more of a high efficiency particulate air (HEPA) filter, a medium filter, a carbon filter, and/or a pretreatment filter.

24. The air treatment device of claim 15, further comprising a wind guide assembly distal to the one or more reactor modules and positioned to receive air therefrom, the wind guide assembly including a cover, and a guide member disposed at least partially within and proximal to the cover.

25. The air treatment device of claim 24, wherein the cover includes a cross-sectional dimension that decreases in a distal direction.

26. A reactor module configured to treat air flowing therethrough, the reactor module comprising:
a housing having an inlet at a first end, an outlet at a second end opposite the first end, and sidewalls extending from the inlet to the outlet along a first axis, the housing having a first dimension along the first axis and a second dimension along a second axis perpendicular to the first axis, wherein the second dimension is longer than the first dimension;
an ultraviolet (UV) light source disposed within the housing, the UV light source extending between opposing ones of the sidewalls; and
a plurality of hollow elongate conduits disposed within the housing and extending between the opposing sidewalls, wherein the individual conduits (i) are radially outward of the UV light source, (ii) extend in a direction parallel to the second axis, and (iii) include a plurality of holes each having a polygon shape, wherein the conduits include a first set of conduits arranged on a first side of the UV light source and a second set of conduits arranged on a second side of the UV light source opposite the first side.

27. The reactor module of claim 26, wherein the housing has an inner surface comprising a reflective material such that, in operation, UV light emitted from the UV light source is reflected internally within the housing.

28. The reactor module of claim 26, wherein the housing has an inner surface comprising chrome or chromium, and wherein the UV light source is configured to emit at least one of UVB wavelengths of 280-315 nanometers (nm) or UVC wavelengths of 100-280 nm.

29. The reactor module of claim 26, wherein the conduits are coated with a solution comprising between 2-4% by weight titanium dioxide, the titanium dioxide including no more than 80% by weight anatase titanium dioxide and a balance of rutile titanium dioxide.

30. The reactor module of claim 26, wherein the holes of the individual conduits have a hexagonal shape, and wherein the conduits comprise a plastic material.

* * * * *